(12) United States Patent
Chang et al.

(10) Patent No.: US 9,587,034 B2
(45) Date of Patent: Mar. 7, 2017

(54) ANTI-MIGE ANTIBODIES THAT BIND TO THE JUNCTION BETWEEN CH4 AND CεMX DOMAINS

(71) Applicant: Academia Sinica, Taipei (TW)

(72) Inventors: Tse Wen Chang, Taipei (TW); Jiun-Bo Chen, Taipei (TW); Chien-Jen Lin, Taipei (TW); Nien-Yi Chen, New Taipei (TW)

(73) Assignee: Academia Sinica, Taipei (TW)

( * ) Notice: Subject to any disclaimer, the term of this patent is extended or adjusted under 35 U.S.C. 154(b) by 59 days.

(21) Appl. No.: 14/395,572

(22) PCT Filed: Mar. 14, 2013

(86) PCT No.: PCT/US2013/031454
§ 371 (c)(1),
(2) Date: Oct. 20, 2014

(87) PCT Pub. No.: WO2013/158274
PCT Pub. Date: Oct. 24, 2013

(65) Prior Publication Data
US 2015/0086558 A1    Mar. 26, 2015

Related U.S. Application Data

(60) Provisional application No. 61/636,618, filed on Apr. 20, 2012.

(51) Int. Cl.
*A61K 39/395* (2006.01)
*C07K 16/42* (2006.01)

(52) U.S. Cl.
CPC ...... *C07K 16/4291* (2013.01); *C07K 2317/24* (2013.01); *C07K 2317/34* (2013.01); *C07K 2317/565* (2013.01); *C07K 2317/73* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 5,079,344 A | 1/1992 | Chang et al. | |
| 5,089,603 A | 2/1992 | Chang | |
| 5,091,313 A | 2/1992 | Chang | |
| 5,231,026 A | 7/1993 | Chang | |
| 5,252,467 A | 10/1993 | Chang | |
| 5,254,671 A | 10/1993 | Chang | |
| 5,260,416 A | 11/1993 | Chang | |
| 5,274,075 A | 12/1993 | Chang | |
| 5,281,699 A | 1/1994 | Chang | |
| 5,292,867 A | 3/1994 | Chang | |
| 5,298,420 A | 3/1994 | Chang | |
| 5,310,875 A | 5/1994 | Chang | |
| 5,342,924 A | 8/1994 | Chang | |
| 5,362,643 A | 11/1994 | Chang | |
| 5,420,251 A | 5/1995 | Chang et al. | |
| 5,422,258 A | 6/1995 | Chang | |
| 5,449,760 A | 9/1995 | Chang | |
| 5,484,907 A | 1/1996 | Chang et al. | |
| 5,514,776 A | 5/1996 | Chang | |
| 5,543,144 A | 8/1996 | Chang | |
| 5,601,821 A | 2/1997 | Stanworth et al. | |
| 5,614,611 A | 3/1997 | Chang | |
| 5,653,980 A | 8/1997 | Hellman | |
| 5,690,934 A | 11/1997 | Chang et al. | |
| 5,866,129 A | 2/1999 | Chang et al. | |
| 5,958,708 A | 9/1999 | Hardman et al. | |
| 6,172,213 B1 | 1/2001 | Lowman et al. | |
| 6,685,939 B2 | 2/2004 | Jardieu et al. | |
| 6,887,472 B2 | 5/2005 | Morsey et al. | |
| 7,897,151 B2 | 3/2011 | Morsey et al. | |
| 8,071,097 B2 | 12/2011 | Wu et al. | |
| 8,137,670 B2 | 3/2012 | Wu et al. | |
| 8,460,664 B2 | 6/2013 | Chang et al. | |
| 8,741,294 B2 | 6/2014 | Chang et al. | |
| 8,974,794 B2 | 3/2015 | Chang et al. | |
| 2009/0010924 A1 | 1/2009 | Wu et al. | |
| 2009/0220416 A1 | 9/2009 | Welt et al. | |
| 2014/0220042 A1 | 8/2014 | Chang et al. | |

FOREIGN PATENT DOCUMENTS

| CN | WO 2010097012 A1 * | 9/2010 | ......... C07K 16/4291 |
|---|---|---|---|
| KR | 10-2012-0019429 A | 3/2012 | |
| WO | WO 89/06138 A1 | 7/1989 | |
| WO | WO 90/15614 A1 | 12/1990 | |
| WO | WO 91/04055 A1 | 4/1991 | |
| WO | WO 91/11456 A1 | 8/1991 | |
| WO | WO 92/07574 A1 | 5/1992 | |
| WO | WO 96/12740 A1 | 5/1996 | |
| WO | WO 98/53843 A1 | 12/1998 | |

(Continued)

OTHER PUBLICATIONS

Janeway et al., Immunobiology, 3rd edition, 1997, Garland Publishing Inc., pp. 3:1-3:11.*
Rudikoff et al., Proc Natl Acad Sci U S A. Mar. 1982;79(6):1979-83.*
Portolano et al., J Immunol. Feb. 1, 1993;150(3):880-7.*
Paul, William E (editor) Fundamental Immunology, 3rd ed. 1993, p. 242.*
Holgate et al., Respir Med. Aug. 2009;103(8):1098-113. doi: 10.1016/j.rmed.2009.03.008. Epub Apr. 10, 2009.*
[No Author Listed] Rituxan® (Rituximab) Proposed Mechanism of Action. Last accessed from http://www.rituxan.com/hem/hcp/mechanism-action/index.html on Oct. 5, 2012.
Achatz et al., Membrane bound IgE: the key receptor to restrict high IgE levels. Open Immunology Journal. 2008;1:25-32.
Batista et al., Characterization and expression of alternatively spliced IgE heavy chain transcripts produced by peripheral blood lymphocytes. J Immunol. Jan. 1, 1995;154(1):209-18.

(Continued)

*Primary Examiner* — Michael Szperka
(74) *Attorney, Agent, or Firm* — Wolf, Greenfield & Sacks, P.C.

(57) ABSTRACT

Antibodies binding to junction regions between the CH4 and CεmX domains of membrane-bound IgE and uses thereof in treating IgE-mediated diseases such as allergic diseases.

23 Claims, 12 Drawing Sheets

(56) References Cited

FOREIGN PATENT DOCUMENTS

| WO | WO 2007/041171 A2 | 4/2007 | |
|---|---|---|---|
| WO | WO 2007/131129 A2 | 11/2007 | |
| WO | WO 2008/116149 A2 | 9/2008 | |
| WO | WO 2008116149 A2 * | 9/2008 | ......... A01K 67/0278 |
| WO | WO 2010/097012 A1 | 9/2010 | |
| WO | WO 2011/108008 A2 | 9/2011 | |

OTHER PUBLICATIONS

Batista et al., Characterization of the human immunoglobulin epsilon mRNAs and their polyadenylation sites. Nucleic Acids Res. Dec. 11, 1995;23(23):4805-11.

Batista et al., The two membrane isoforms of human IgE assemble into functionally distinct B cell antigen receptors. J Exp Med. Dec. 1, 1996;184(6):2197-205.

Benhamou et al., Anti-immunoglobulins induce death by apoptosis in WEHI-231 B lymphoma cells. Eur J Immunol. Jun. 1990;20(6):1405-7.

Berard et al., Activation sensitizes human memory B cells to B-cell receptor-induced apoptosis. Immunology. Sep. 1999;98(1):47-54.

Bozelka et al., IgE isotype suppression in anti-epsilon-treated mice. Immunology. Jul. 1982;46(3):527-32.

Brightbill et al., Antibodies specific for a segment of human membrane IgE deplete IgE-producing B cells in humanized mice. J Clin Invest. Jun. 2010;120(6):2218-29.

Caraux et al., Surface immunoglobulins as targets for anti-immunoglobulin-dependent cell-mediated lysis of B cells. Cell Immunol. Mar. 1983;76(2):372-8.

Chan et al., The novel human IgE epsilon heavy chain, epsilon tailpiece, is present in plasma as part of a covalent complex. Mol Immunol. Apr. 2000;37(5):241-52.

Chang et al., Anti-IgE antibodies for the treatment of IgE-mediated allergic diseases. Adv Immunol. 2007;93:63-119.

Chang et al., Monoclonal antibodies specific for human IgE-producing B cells: a potential therapeutic for IgE-mediated allergic diseases. Biotechnology (N Y). Feb. 1990;8(2):122-6.

Chang, Developing antibodies for targeting immunoglobulin and membrane-bound immunoglobulin E. Allergy Asthma Proc. Mar.-Apr. 2006;27(2 Suppl 1):S7-14.

Chang, The pharmacological basis of anti-IgE therapy. Nat Biotechnol. Feb. 2000;18(2):157-62.

Chen et al., Controlling IgE production by targeting membrane-bound IgE on B Cells. Jun. 19, 1991. Chapter s 1-4. 76 pages.

Chen et al., Monoclonal antibodies against the C(epsilon)mX domain of human membrane-bound IgE and their potential use for targeting IgE-expressing B cells. Int Arch Allergy Immunol. Aug. 2002;128(4):315-24.

Chen et al., Unique epitopes on C epsilon mX in IgE-B cell receptors are potentially applicable for targeting IgE-committed B cells. J Immunol. Feb. 15, 2010;184(4):1748-56. Epub Jan. 18, 2010.

Chinn et al., Antibody therapy of non-Hodgkin's B-cell lymphoma. Cancer Immunol Immunother. May 2003;52(5):257-80. Epub Feb. 28, 2003.

Chowdhury et al., Targeting the junction of CεmX and ε-migis for the specific depletion of mIgE-expressing B cells. Mol Immunol. Oct. 2012;52(3-4):279-88. Epub Jun. 29, 2012.

Davis et al., An epitope on membrane-bound but not secreted IgE: implications in isotype-specific regulation. Biotechnology (N Y). Jan. 1991;9(1):53-6.

Davis et al., Can anti-IgE be used to treat allergy? Springer Semin Immunopathol. 1993;15(1):51-73.

Disis et al., Granulocyte-macrophage colony-stimulating factor: an effective adjuvant for protein and peptide-based vaccines. Blood. Jul. 1, 1996;88(1):202-10.

Donjerković et al., Activation-induced cell death in B lymphocytes. Cell Res. Sep. 2000;10(3): 179-92.

Eray et al., Cross-linking of surface IgG induces apoptosis in a bcl-2 expressing human follicular lymphoma line of mature B cell phenotype. Int Immunol. Dec. 1994;6(12):1817-27.

Feichtner et al., Targeting the extracellular membrane-proximal domain of membrane-bound IgE by passive immunization blocks IgE synthesis in vivo. J Immunol. Apr. 15, 2008;180(8):5499-505.

Genbank Submission; NIH/NCBI, Accession No. AER46505.1, Kuwata, Nov. 6, 2011, 2 pages.

Genbank Submission; NIH/NCBI, Accession No. BAE71466.1, Furukawa et al., Jan. 6, 2006, 2 pages.

Genbank Submission; NIH/NCBI, Accession No. S17626, Clackson et al., Jan. 21, 2000, 2 pages.

Genbank Submission; NIH/NCBI, Accession No. S45714, Kim et al., May 7, 1999, 3 pages.

Grafton et al., Mechanisms of antigen receptor-dependent apoptosis of human B lymphoma cells probed with a panel of 27 monoclonal antibodies. Cell Immunol. Nov. 25, 1997;182(1):45-56.

Haak-Frendscho et al., Administration of an anti-IgE antibody inhibits CD23 expression and IgE production in vivo. Immunology. Jun. 1994;82(2):306-13.

Haba et al., Inhibition of IgE synthesis by anti-IgE: role in long-term inhibition of IgE synthesis by neonatally administered soluble IgE. Proc Natl Acad Sci U S A. May 1990;87(9):3363-7.

Hung et al., Alleles and isoforms of human membrane-bound IgA1. Mol Immunol. Aug. 2008;45(13):3624-30. Epub Jun. 6, 2008.

Inführ et al., Molecular and cellular targets of anti-IgE antibodies. Allergy. Aug. 2005;60(8):977-85.

Janeway et al., Immunobiology: the immune system in health and disease. 6$^{th}$ edition. 2005:352-353, 401-402.

Kass et al., Induction of protective host immunity to carcinoembryonic antigen (CEA), a self-antigen in CEA transgenic mice, by immunizing with a recombinant vaccinia-CEA virus. Cancer Res. Feb. 1, 1999;59(3):676-83.

Lin et al., CεmX peptide-carrying HBcAg virus-like particles induced antibodies that down-regulate mIgE-B lymphocytes. Mol Immunol. Oct. 2012;52(3-4):190-9.

Lorenzi et al., Sequence-specific antibodies against human IgE isoforms induced by an epitope display system. Immunotechnology. Mar. 1999;4(3-4):267-72.

Lyczak et al., Expression of novel secreted isoforms of human immunoglobulin E proteins. J Biol Chem. Feb. 16, 1996;271(7):3428-36.

MacGlashan, IgE-dependent signaling as a therapeutic target for allergies, Trends in Pharmacological Sciences, 2012, vol. 33, No. 9, pp. 502-209. See Abstract.

Major et al., Structural features of the extracellular portion of membrane-anchoring peptides on membrane-bound immunoglobulins. Mol Immunol. Feb. 1996;33(2):179-87.

Martin et al., B cell immunobiology in disease: evolving concepts from the clinic. Annu Rev Immunol. 2006;24:467-96.

Mathas et al., Anti-CD20- and B-cell receptor-mediated apoptosis: evidence for shared intracellular signaling pathways. Cancer Res. Dec. 15, 2000;60(24):7170-6.

Parry et al., Hypercross-linking surface IgM or IgD receptors on mature B cells induces apoptosis that is reversed by costimulation with IL-4 and anti-CD40. J Immunol. Mar. 15, 1994;152(6):2821-9.

Peng et al., A new isoform of human membrane-bound IgE. J Immunol. Jan. 1, 1992;148(1):129-36.

Poggianella et al., The extracellular membrane-proximal domain of human membrane IgE controls apoptotic signaling of the B cell receptor in the mature B cell line A20. J Immunol. Sep. 15, 2006;177(6):3597-605.

Takamuku et al., Apoptosis in antibody-dependent monocyte-mediated cytotoxicity with monoclonal antibody 17-1A against human colorectal carcinoma cells: enhancement with interferon gamma. Cancer Immunol Immunother. Dec. 1996;43(4):220-5.

Talay et al., IgE$^+$ memory B cells and plasma cells generated through a germinal-center pathway. Nat Immunol. Feb. 26, 2012;13(4):396-404.

Timmerman et al., Linkage of foreign carrier protein to a self-tumor antigen enhances the immunogenicity of a pulsed dendritic cell vaccine. J Immunol. May 1, 2000;164(9):4797-803.

(56) References Cited

OTHER PUBLICATIONS

Wagner et al., Monoclonal anti-equine IgE antibodies with specificity for different epitopes on the immunoglobulin heavy chain of native IgE, Veterinary Immunology and Immunopathology, 2003, vol. 92, No. 1, pp. 45-60.
Wan et al., Genetic variations in the C epsilon mX domain of human membrane-bound IgE. Immunogenetics. May 2010;62(5):273-80. Epub Mar. 24, 2010.
Yu et al., Two isoforms of human membrane-bound alpha Ig resulting from alternative mRNA splicing in the membrane segment. J Immunol. Dec. 1, 1990;145(11):3932-6.
Zhang et al., Complex alternative RNA splicing of epsilon-immunoglobulin transcripts produces mRNAs encoding four potential secreted protein isoforms. J Biol Chem. Jan. 7, 1994;269(1):456-62.
Zhang et al., Two unusual forms of human immunoglobulin E encoded by alternative RNA splicing of epsilon heavy chain membrane exons. J Exp Med. Jul. 1, 1992;176(1):233-43.
Chu et al., Two potential therapeutic antibodies bind to a peptide segment of membrane-bound IgE in different conformations. Nat Commun 2014;5:3139. doi: 10.1038/ncomms4139.

\* cited by examiner

| P1    | SVNPGLAGGSAQSQRAPDRVL |
|-------|-----------------------|
| P1.15 | SVNPGLAGGSAQS         |
| P1.17 | VNPGLAGGSAQS          |
| P1.18 | NPGLAGGSAQS           |
| P1.19 | PGLAGGSAQS            |

B

| CcmX-fusion partner | Junction Residues |
|---------------------|-------------------|
| IgE.Fc-ccm67        | SVNPGLAGGSAQS     |
| IgG.Fc-ccm67        | SPGKGLAGGSAQS     |
| HBcAg-P1            | SVNPGLAGGSAQS     |
| HBcAg-CcmX          | GGGGTLAGGSAQS     |

Fig. 6

V_H domain

```
                      10                  20                  30
2H9          QVQMQQPGAELVRPGASVKMSCRTSGYTFT
HVI          QAYLQQSGAELVRPGASVKMSCKASGYTFT 40              50  52a
2H9          NYNVHWLKQTPGQGLEWIGGMYPGNDDILY
HVI          SYNMHWVKQTPRQGLEWIGAIYPGNGDTSY 70              80  82abc
2H9          NQNFKDRATLTADRSSSTAYIQLRSLTSED
HVI          NQKFKGKATLTVDKSSSTAYMQLSSLTSED 92      100ab            110
2H9          SAVYYCTRSGLQGPWFDYWGQGTLVTVSA
HVI/HD3/HJ3  SAVYFCARSGQLGLWFAYWGQGTLVTVSA
```

V_L domain

```
                      10                  20                  30
2H9          DIQMTQSSSYLSVSLGGRVTISCRASDHIN
KV13         DIQMTQSSSYLSVSLGGRVTITCKASDHIN 40                  50                  60
2H9          NWLAWYQQKPGNAPRLLISSATSLETGVPS
KV13         NWLAWYQQKPGNAPRLLISGATSLETGVPS 70                  80                  90
2H9          RFSGSGSGKDYSLTIISVQTEDVATYYCQQ
KV13         RFSGSGSGKDYTLSITSLQTEDVATYYCQQ 100
2H9          CWITPFTFGSGTKLEIK
KV13/KJ4     YWSTPFTFGSGTKLEIK
```

Figure 7

V<sub>H</sub> domain

```
                10                  20                  30
5A8     Q V Q L K Q S G P G L V A P S Q S L S I T C T V S G F S L T
HV2     Q V Q L K E S G P G L V A P S Q S L S I T C T V S G F S L T 40                  50
5A8     D Y G V N W V R Q P P G K G L E W L G M I W G D G S T D Y N
HV2     G Y G V N W V R Q P P G K G L E W L G M I W G D G S T D Y N 60                  70              80  82 a b c
5A8         S T L K S R L S I S K D N S K S Q V F L K I N S L Q T D D T
HV2         S A L K S R L S I S K D N S K S Q V F L K M N S L Q T D D T 90                  100
5A8         A R Y Y C A L N W F A Y W G Q G T L V T A A A
HV2/HD1/HJ3 A R Y Y C A R N W F A Y W G Q G T L V T A A A
```

V<sub>L</sub> domain

```
                10                  20                  31 a
5A8     N I V M T Q S P A I M S A S P G E K V T M T C S A S S S V N
KV4     Q I V L T Q S P A I M S A S P G E K V T M T C S A S S S V S 40                  50                  60
5A8     Y M H W Y Q Q K S G T S P K R W I Y D T S K L A S G V P A R
KV4     Y M H W Y Q Q K S G T S P K R W I Y D T S K L A S G V P A R 70                  80
5A8     F S G S G S G T S Y S L T I S S M E A E D A A T Y Y C Q Q W
KV4     F S G S G S G T S Y S L T I S S M E A E D A A T Y Y C Q Q W 100         106 a
5A8         S S N P W T F G G G T K L E I K
KV4/KJ1     S S N P P T F G G G T K L E I K
```

ANTI-MIGE ANTIBODIES THAT BIND TO THE JUNCTION BETWEEN CH4 AND CεMX DOMAINS

RELATED APPLICATION

This application is a national stage filing under 35 U.S.C. §371 of international PCT application PCT/US2013/031454, filed Mar. 14, 2013, which claims priority to U.S. provisional application under serial No. 61/636,618, filed on Apr. 20, 2012, the entire content of which is herein incorporated by reference.

BACKGROUND OF THE INVENTION

Immunoglobulin E (IgE) plays a central role in mediating type I hypersensitivity reactions that are responsible for causing allergic diseases, including allergic asthma, allergic rhinitis, atopic dermatitis, peanut allergy, latex allergy, and others. Allergic reactions are the responses of the immune system toward harmless environmental substances, such as dust mites, tree and grass pollens, certain food and drugs, and bee and fire ant bites. In such reactions, the binding of an allergen to IgE on the surface of basophils and mast cells causes the cross-linking of IgE and the aggregation of the underlying receptors of IgE.Fc, the type I IgE.Fc receptors, or FcεRI. This receptor aggregation subsequently activates the signaling pathway leading to the exocytosis of granules and the release of pharmacologic mediators, such as histamine, leukotrienes, tryptase, cytokines and chemokines. The release of those mediators from mast cells and basophils causes the various pathological manifestations of allergy.

Anti-IgE antibodies binding to free IgE in the blood and in interstitial fluid and to mIgE on B cells, but not to IgE bound by FcεRI on basophils and mast cells, such as omalizumab and TNX-901, have been developed for treating IgE-mediated allergic diseases. These antibodies bind to IgE with high affinity at a site in the CH3 domain of Fc that overlaps with the binding site of FcεRI. Hence, the anticipated therapeutic effects of these antibodies are based on the binding of the antibodies to free IgE and to mIgE on B lymphoblasts and on memory B cells, which leads to the reduction of overall free IgE level in blood and interstitial fluid.

The clinical development of omalizumab (trade name Xolair) has shown additional multiple pharmacologic effects in attenuating type I hypersensitivity in various allergic indications. The binding of anti-IgE to free IgE further prevents IgE binding to FcεRI on the surface of basophils and mast cells. As the FcεRI unoccupied by IgE is unstable and subsequently internalized and degraded, the depletion of free IgE with anti-IgE binding also gradually down-regulates FcεRI on basophils and mast cells. Evidence for other effects of the antibody therapy has been found, including the neutralization of cytokinergic activities, the attenuation of overall inflammatory activity, and possibly the sweeping of allergens through the accumulation of IgE-anti-IgE immune complexes.

CεmX is a 52-amino acid segment located between the CH4 domain and the C-terminal membrane-anchoring segment of human membrane-bound ε chain (mε). It has been shown that in most human subjects studied, the mε without CεmX (mεS) accounts for minute proportions, whereas mε chain with CεmX (mεL) is dominantly expressed. The mRNAs for ε chain of free, secreted IgE and for mεS and mεL of mIgE are all derived from alternative splicing of the ε RNA transcript. The amino acid and nucleotide sequences of CεmX are unique in the entire protein and DNA databases. Therefore, CεmX provides a unique antigenic site for targeting mIgE and the mIgE-expressing B cells. Anti-IgE antibodies binding to the CεmX (also known as M1' region), which exists on human mIgE for the targeting of mIgE-expressing B lymphocytes, have also been developed, e.g., a20. Chen et al., *J. Immunol.*, 2010; 184; 1748-1756, U.S. Pat. No. 8,071,097; and International Publication No. WO2010/097012.

It is of great interest to identify new antigenic epitopes involving the CεmX domain and develop new therapeutic antibodies binding to such antigenic epitopes.

SUMMARY OF THE INVENTION

This present disclosure pertains to the development and identification of antibodies that are specific to junction regions between the CH4 domain and CεmX domain of the long isoform of ε chain of human mIgE on human B lymphocytes. The long isoform of mε chain, containing a 52-aa CεmX domain between the CH4 domain and membrane-anchor segment, is much more abundant than the short or conventional isoform of mε chain, which does not contain the CεmX domain, on human mIgE-expressing B lymphocytes. The present disclosure also pertains to the utility of such antibodies in treating allergic diseases and other diseases that are mediated by IgE.

Accordingly, one aspect of the present disclosure features an isolated anti-IgE antibody binding to an epitope of a membrane-bound IgE (mIgE). The epitope consists of a first portion and a second portion, the first portion being located in the CH4 domain of the mIgE, e.g., TVQRAVSVNP (SEQ ID NO:12) or a fragment thereof, and the second portion being located in the CεmX domain of the mIgE, e.g., GLAGGSAQSQ (SEQ ID NO:13), or a fragment thereof. In some embodiments, the anti-IgE antibody described herein binds to SVNPGLAGGSAQS (SEQ ID NO:11).

In some examples, the anti-IgE antibody comprises a heavy chain variable region ($V_H$) that contains a $V_H$ complementarity determining region (CDR) 1 of GYTFTNYNVH (SEQ ID NO:8), a $V_H$ CDR2 of GMYPGNDDILYNQNFKD (SEQ ID NO:9), and a $V_H$ CDR3 of SGLQGPWFDY (SEQ ID NO:10). Alternatively or in addition, the anti-IgE antibody comprises a light chain variable region ($V_L$) that contains a $V_L$ CDR1 of RASDHINNWLA (SEQ ID NO:5), a $V_L$ CDR2 of SATSLET (SEQ ID NO:6), and a $V_L$ CDR3 of QQCWITPFT (SEQ ID NO:7).

Alternatively or in addition, the anti-IgE antibody comprises a heavy chain variable region at least 85% (e.g., 90%, 95%, 97%, 98%, or 99%) identical to SEQ ID NO:3, and/or a light chain variable region at least 85% (e.g., 90%, 95%, 97%, 98%, or 99%) identical to SEQ ID NO:4. The anti-IgE antibody can comprises a heavy chain variable region set forth as SEQ ID NO:3 and a light chain variable region set forth as SEQ ID NO:4. Alternatively, the antibody binds to the same epitope as an antibody comprising a heavy chain variable region set forth as SEQ ID NO:3 and a light chain variable region set forth as SEQ ID NO:4, e.g., mAb 2H9.

In some examples, the anti-IgE antibody comprises a heavy chain variable region ($V_H$) that contains a $V_H$ CDR1 of GFSLTDYGVN (SEQ ID NO:19), a $V_H$ CDR2 of MIWGDGSTDYNSTL (SEQ ID NO:20), and a $V_H$ CDR3 of NWFAY (SEQ ID NO:21). Alternatively or in addition, such an anti-IgE antibody comprises a light chain variable region ($V_L$) comprising and a $V_L$ CDR1 of SSSVNYMH (SEQ ID NO:22), a $V_L$ CDR2 of DTSKLAS (SEQ ID NO:23), and a $V_L$ CDR3 of QQWSSNPW (SEQ ID NO:24).

Alternatively or in addition, the anti-IgE antibody comprises a heavy chain variable region at least 85% (e.g., 90%, 95%, 97%, 98%, or 99%) identical to SEQ ID NO:17, and/or a light chain variable region at least 85% (e.g., 90%, 95%, 97%, 98%, or 99%) identical to SEQ ID NO:18. The anti-IgE antibody can comprises a heavy chain variable region set forth as SEQ ID NO:17 and a light chain variable region set forth as SEQ ID NO:18. Alternatively, the antibody binds to the same epitope as an antibody comprising a heavy chain variable region set forth as SEQ ID NO:17 and a light chain variable region set forth as SEQ ID NO:18, e.g., mAb 5A8.

Any of the ant-IgE antibodies described herein can be a full length antibody or an antigen-binding fragment thereof. In some examples, the antibodies are human antibodies or humanized antibodies.

Another aspect of the present disclosure features a method for treating an IgE-associated disease, comprising administering to a subject in need thereof any of the anti-IgE antibodies described above, e.g., an anti-IgE antibody binding to SVNPGLAGGSAQS (SEQ ID NO:11) or binding to the same epitope as mAb 2H9, which comprises a heavy chain variable region set forth as SEQ ID NO:3 and a light chain variable region set forth as SEQ ID NO:4, or mAb 5A8, which comprises a heavy chain variable region set forth as SEQ ID NO:17 and a light chain variable region set forth as SEQ ID NO:18.

In some examples, the subject (e.g., a human patient) in need of the treatment is diagnosed with, suspected of having, or at risk for the IgE-mediated disease. The IgE-mediated disease can be an allergic disease. Examples include, but are not limited to, anaphylaxis, allergic asthma, allergic rhinitis, atopic dermatitis (eczema), dust allergy, insect or reptile venom allergy, food allergy, pollen allergy, and latex allergy.

In yet another aspect, the present disclosure features an isolated nucleic acid encoding the heavy chain and/or light chain of the anti-IgE antibodies described herein. In one example, the isolated nucleic acid comprises an nucleotide sequence encoding an antibody heavy chain variable region that contains a $V_H$ CDR 1 of GYTFTNYNVH (SEQ ID NO:8), a $V_H$ CDR2 of GMYPGNDDILYNQNFKD (SEQ ID NO:9), and a $V_H$ CDR3 of SGLQGPWFDY (SEQ ID NO:10). Such a nucleotide sequence (e.g., SEQ ID NO:1) can encode the antibody heavy chain variable region of SEQ ID NO:3.

In another example, the isolated nucleic acid comprises an nucleotide sequence encoding an antibody heavy chain variable region that contains a $V_H$ CDR1 of GFSLTDYGVN (SEQ ID NO:19), a $V_H$ CDR2 of MIWGDGSTDYNSTL (SEQ ID NO:20), and a $V_H$ CDR3 of NWFAY (SEQ ID NO:21). Such a nucleotide sequence can encode the antibody heavy chain variable region of SEQ ID NO:17.

Alternatively or in addition, the isolated nucleic acid comprises a nucleotide sequence encoding an antibody $V_L$ chain that contains a $V_L$ CDR1 of RASDHINNWLA (SEQ ID NO:5), a $V_L$ CDR2 of SATSLET (SEQ ID NO:6), and a $V_L$ CDR3 of QQCWITPFT (SEQ ID NO:7). Such a nucleotide sequence (e.g., SEQ ID NO:2) can encode the antibody light chain variable region of SEQ ID NO:4.

In other examples, the isolated nucleic acid comprises a nucleotide sequence encoding an antibody $V_L$ chain that contains a $V_L$ CDR1 of SSSVNYMH (SEQ ID NO:22), a $V_L$ CDR2 of DTSKLAS (SEQ ID NO:23), and a $V_L$ CDR3 of QQWSSNPW (SEQ ID NO:24). Such a nucleotide sequence can encode the antibody light chain variable region of SEQ ID NO:18.

In still another aspect, the present disclosure features a vector (e.g., an expression vector) comprising one or more of the nucleic acids described herein, e.g., a nucleic acid encoding the antibody heavy chain variable region as described herein and/or a nucleic acid encoding the antibody light chain variable region as described herein. Host cells comprising the vectors described herein are also within the scope of this disclosure.

In addition, the present disclosure provides an immune composition comprising a peptide and an adjuvant, wherein the peptide comprises the amino acid sequence of SVNPGLAGGSAQS (SEQ ID NO:11) or an immunogenic epitope therein, and uses of the immune composition for inducing immune responses specific to SEQ ID NO:11, such as antibody production.

Also within the scope of the present disclosure are pharmaceutical compositions for use in treating an IgE-mediated disease, such as an allergic disease (e.g., anaphylaxis, allergic asthma, allergic rhinitis, atopic dermatitis (eczema), dust allergy, insect or reptile venom allergy, food allergy, pollen allergy, and latex allergy), the pharmaceutical composition comprising any of the anti-IgE antibodies or nucleic acid encoding such and a pharmaceutically acceptable carrier, and uses of such pharmaceutical compositions in manufacturing a medicament for treating the IgE-mediated disease.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 6 shows the amino acid sequences of mAb 2H9 and the sequences of a murine heavy chain subgroup 1 (HV1) and light chain k subgroup 13 (KV13). The three CDRs in each chain are underlined. 2H9 heavy chain variable region: SEQ ID NO:3; 2H9 light chain variable region: SEQ ID NO:4; HV1: SEQ ID NO:31; and KV13: SEQ ID NO:32.

FIG. 7 shows sequence alignments between the $V_H$ of mAb 5A8 (SEQ ID NO:17) and murine consensus sequences of heavy chain subgroup 1 (HV2; SEQ ID NO:33) and between the $V_L$ of mAb 5A8 (SEQ ID NO:18) and the light chain k subgroup 13 (KV4; SEQ ID NO:34). The three CDRs in each chain are underlined.

DETAILED DESCRIPTION OF THE INVENTION

Figure 1:
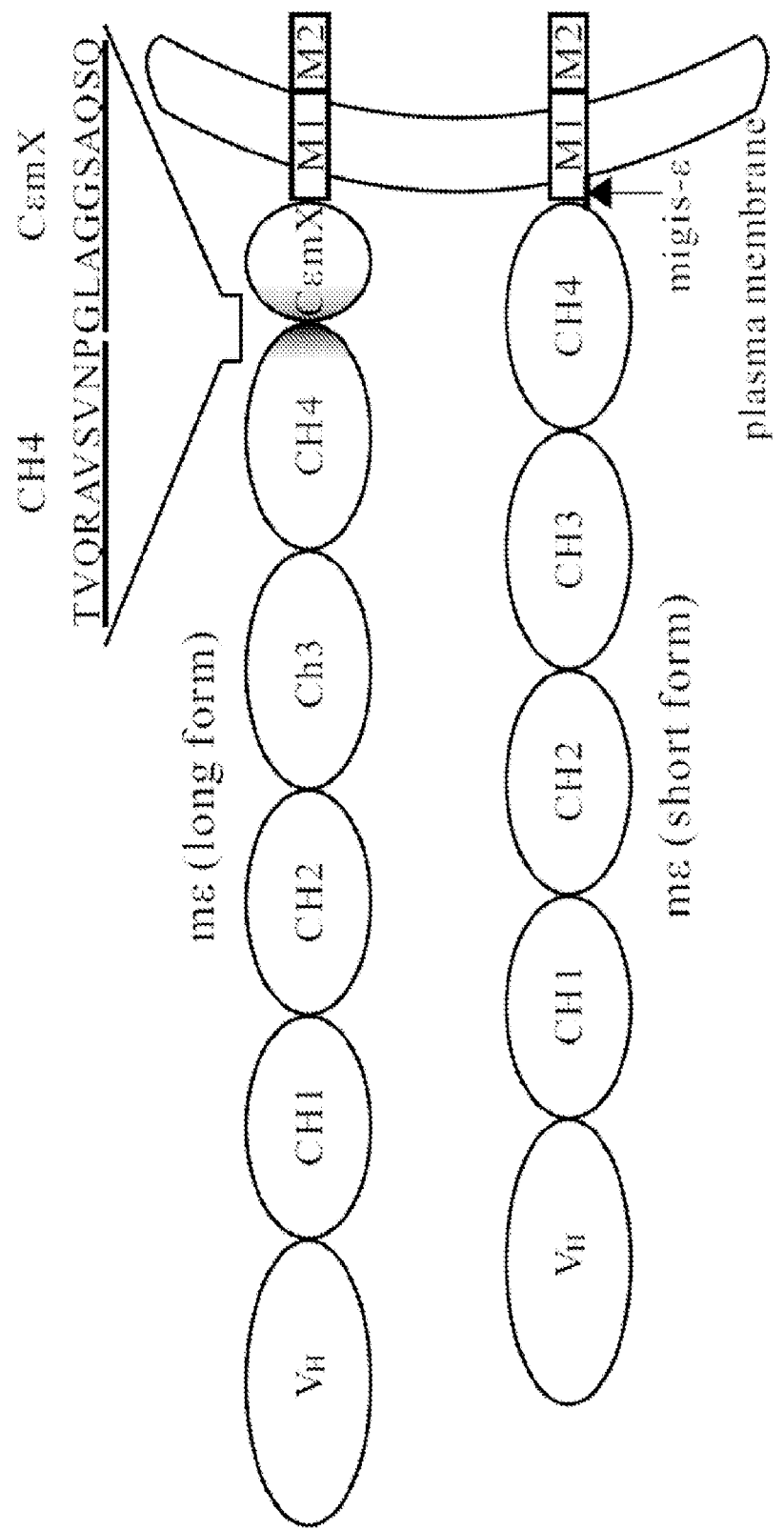
FIG. 1 is a schematic representation of human ε-chain, the long, short isoforms of mε chain, and the junction residues (grey shaded) between the CH4 domain and CεmX domain of the long form of mε. TVQRAVSVNP (SEQ ID NO:12) is the C-terminal segment of CH4 and GLAGGSAQSQ (SEQ ID NO:13) is the N-terminal segment of CεmX.

Several anti-IgE antibodies have been developed and their binding epitopes in mIgE have been determined. See, e.g., US2009/0010924, WO2010/097012, U.S. Pat. No. 8,071, 097, Brightbill et al. *Journal of Clinical Investigation* 120: 2218-29 (2010), Chen et al., *Journal of Immunology,* 184: 1748-56 (2010). All these anti-IgE antibodies were found to bind to epitopes located entirely inside the CεmX domain.

The present disclosure is based on the development of anti-IgE antibodies binding to newly identified antigenic epitopes located at the junction of the CH4 and CεmX domains and the unexpected discoveries that such antibodies are capable of inducing apoptosis and antibody-dependent cell cytotoxicity (ADCC) in B cells expressing mIgE. These results indicate that antibodies binding to such junction regions between the CH4 and CεmX domains are effective in treating IgE-mediated diseases via at least the elimination of mIgE-expressing B cells.

Accordingly, the present disclosure pertains to the development of antibodies capable of binding to (e.g., specifically binding to) an epitope located at both the CH4 domain and CεmX domain (e.g., at the junction of these two domains) of the long isoform of ε chain of human mIgE, which can be expressed on human B lymphocytes. In particular, such antibodies recognize an epitope consisting of a first portion and a second portion, wherein the first portion contains part of the CH4 domain (e.g., the C-terminus of the CH4 domain) and the second portion contains part of the CεmX domain (e.g., the N-terminus of the CεmX domain). Also provided here are uses of the anti-IgE antibodies described herein for treating IgE-mediated diseases such as allergic diseases, nucleic acid molecules encoding the anti-IgE antibodies, vectors (e.g., expression vectors) comprising such nucleic acids, host cells comprising the vectors (e.g., for producing the anti-IgE antibodies described here). Also within the scope of this disclosure are immune peptides that comprise the newly identified junction antigenic epitopes and uses thereof in inducing immune responses specific to such epitopes.

Anti-IgE Antibodies

An antibody (interchangeably used in plural form) is an immunoglobulin molecule capable of binding to a target antigen, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The isolated anti-IgE antibodies described herein are capable of binding to an epitope containing both residues located in the CH4 domain and residues located in the CεmX domain of a membrane-bound IgE molecule, which can be expressed on the surface of B cells (e.g., human B cells). The term "isolated antibody" used herein refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC.

The amino acid sequence (SEQ ID NO:16) of the CH4-CεmX domains of human mIgE is provided below:

```
GPRAAPEVYA FATPEWPGSR DKRTLACLIQ NFMPEDISVQ

WLHNEVQLPD ARHSTTQPRK TKGSGFFVFS RLEVTRAEWE

QKDEFICRAV HEAASPSQTV QRAVSVNPGL AGGSAQSQRA

PDRVLCHSGQ QQGLPRAAGG SVPHPRCHCG AGRADWPGPP
```

The bold-faced amino acid residues represent the sequence of the CϵmX domains.

In some embodiments, the anti-IgE antibody described herein binds to a linear epitope consisting of one portion derived from the CH4 domain (e.g., the C-terminus of the CH4 domain) and the other portion derived from the CϵmX domain (e.g., the N-terminus of the CϵmX domain). A linear epitope is presented by amino acid residues in one stretch of peptide, typically 6-15 aa in length, in a protein molecule. A linear epitope is rarely longer than 15 aa in length. A peptide segment as short as of 30-50 aa in length potentially contain several or many discrete epitopes, each of which is defined by the specific reactivity with a monoclonal antibody or a set of polyclonal antibodies.

In some examples, the anti-IgE antibody described herein is capable of binding to a linear epitope consisting of two segments, the first one being derived from the C-terminus of the CH4 domain and the second one being derived from the N-terminus of the CϵmX domain. This linear epitope can consist of 6-15 amino acid residues (e.g., 6-12 aa, 6-10 aa, 8-15aa, or 8-10aa) located at the junction of the CH4 and CϵmX domains. In some examples, the linear epitope has 6, 7, 8, 9, 10, 11, 12, 13, 14, or 15 amino acids in length.

The first segment can comprise the amino acid sequence TVQRAVSVNP (SEQ ID NO:12) or a fragment thereof (e.g., having a deletion of 1, 2, 3, 4, 5, 6 or more residues from the N-terminal end), which is located at the C-terminus of the CH4 domain. In one example, the first segment from the C-terminus of the CH4 domain includes the sequence SVNP (SEQ ID NO:14) or a fragment thereof (e.g., having a deletion of 1, 2, or 3 residues from the N-terminal end).

The second segment can comprise the amino acid sequence GLAGGSAQSQRAPDRVL (SEQ ID NO:35), or a fragment thereof (e.g., having a deletion of 1, 2, 3, 4, 5, 6, 7, 8, 9, 10 or more residues from the C-terminal end). In one example, the second segment includes the amino acid sequence GLAGGSAQS (SEQ ID NO:15), or a fragment thereof (e.g., having a deletion of 1, 2, or 3 residues from the C-terminal end).

In some embodiments, the anti-IgE antibodies described herein bind to the peptide SVNPGLAGGSAQS (SEQ ID NO:11) or a fragment thereof, e.g., VNPGLAGGSAQS (SEQ ID NO:26) or NPGLAGGSAQS (SEQ ID NO:27).

Alternatively, the anti-IgE antibodies described herein can bind to a conformational epitope that contain amino acid residues located in both the CH4 and CϵmX domains. A conformational epitope is formed by amino acid residues residing on two or more than two parts of the polypeptide chain(s) of a protein molecule.

The anti-IgE antibodies described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in *Eur. J. Immunol.* (1999) 29:2613-2624; PCT Application No. PCT/GB99/01441; and/or UK Patent Application No. 9809951.8.

Any of the anti-IgE antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In one example, the anti-IgE antibody described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the anti-IgE antibody disclosed herein specifically binds any of the CH4/CϵmX epitopes described herein, such as the linear epitopes noted above and elsewhere in this specification. An antibody that "specifically binds" to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen or an epitope than it does with alternative targets/epitopes. An antibody "specifically binds" to a target antigen if it binds with greater affinity, avidity, more readily, and/or with greater duration than it binds to other substances. For example, an antibody that specifically (or preferentially) binds to an IgE epitope is an antibody that binds this IgE epitope with greater affinity, avidity, more readily, and/or with greater duration than it binds to other IgE epitopes or non-IgE epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

The anti-IgE antibody described herein can induce apoptosis and/or ADCC effects in B cells expressing mIgE, thereby effective in eliminating such B cells and treating IgE-mediated diseases such as allergic diseases. In some examples, the anti-IgE antibody described herein can eliminate at least 20%, at least 40%, at least 50%, at least 75%, at least 90%, or at least 95%, mIgE-expressing B cells in a subject (e.g., a human patient).

The binding affinity of the anti-IgE antibody described herein to its cognate epitope or mIgE molecules expressed on B cells can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to an IgE epitope is by measuring binding affinity of monofunctional Fab fragments of the antibody. To obtain monofunctional Fab fragments, an antibody (for example, IgG) can be cleaved with papain or expressed recombinantly. The affinity of an anti-IgE Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IgE, and does not significantly bind an IgE molecule from another mammalian species. In some embodiments, the antibody binds human IgE as well as one or more IgE from another mammalian species.

Provided below is a specific example of the anti-IgE antibody described herein.

Anti-IgE Antibodies 2H9 and 5A8, and Functional Variants Thereof

Figure 2:
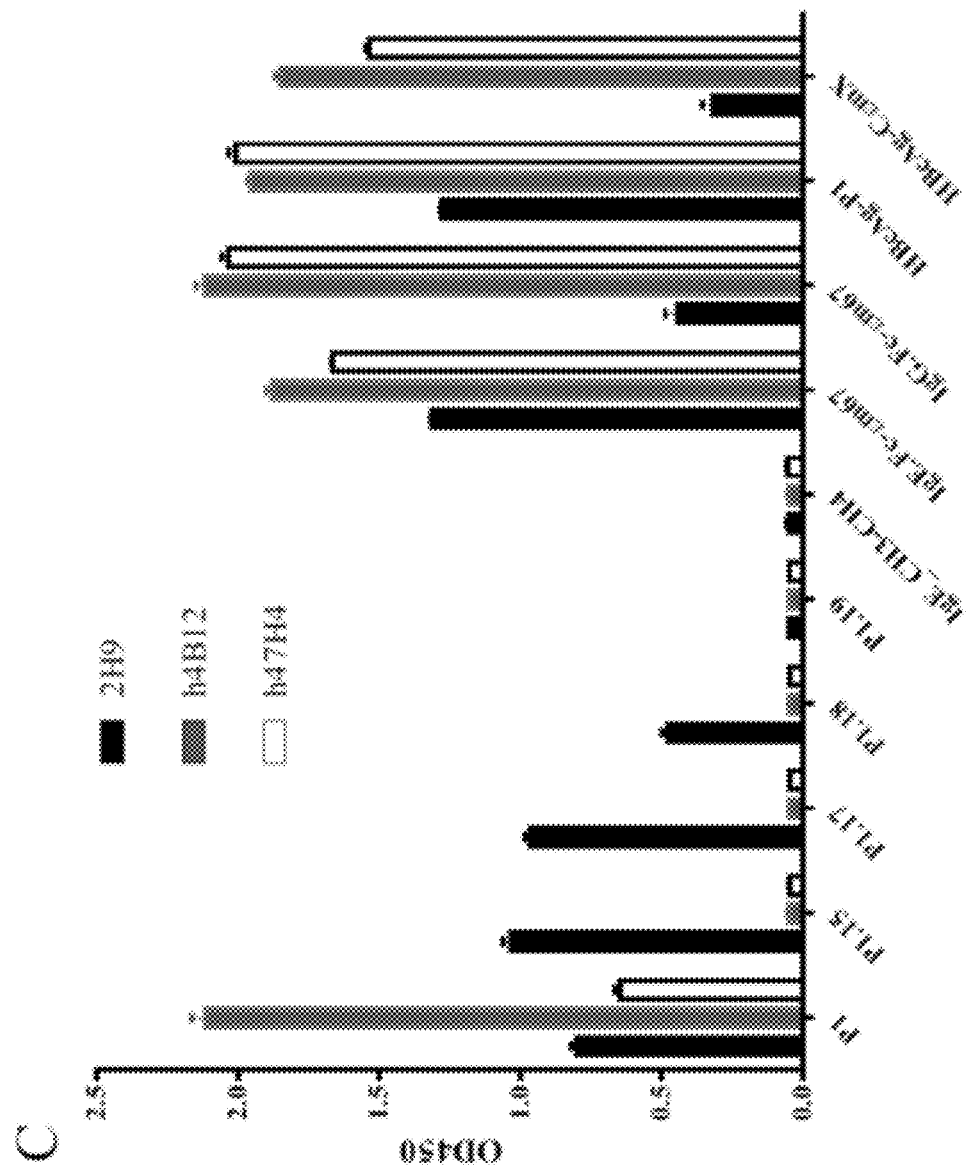
FIG. 2 shows epitope mapping of monoclonal anti-IgE antibody mAb 2H9. A: synthetic peptides representing the junction of CH4-CεmX. P1: SEQ ID NO:25; P1.15: SEQ ID NO:11; P1.17:SEQ ID NO:36; P1.18: SEQ ID NO:27; and P1.19: SEQ ID NO:28. B: Various CεmX-fusion proteins and amino acid sequences of junction residues. IgE.Fc-εm67 junction sequence: SEQ ID NO:11; IgG.Fc-εm67 junction sequence: SEQ ID NO:29; HBcAg-P1 junction sequence: SEQ ID NO:11; and HBcAg-CεmX: SEQ ID NO:30. C: a chart showing binding activities of monoclonal antibodies 2H9, h4B12, and h47H4 to various junction peptides and recombinant proteins.
Figure 3:
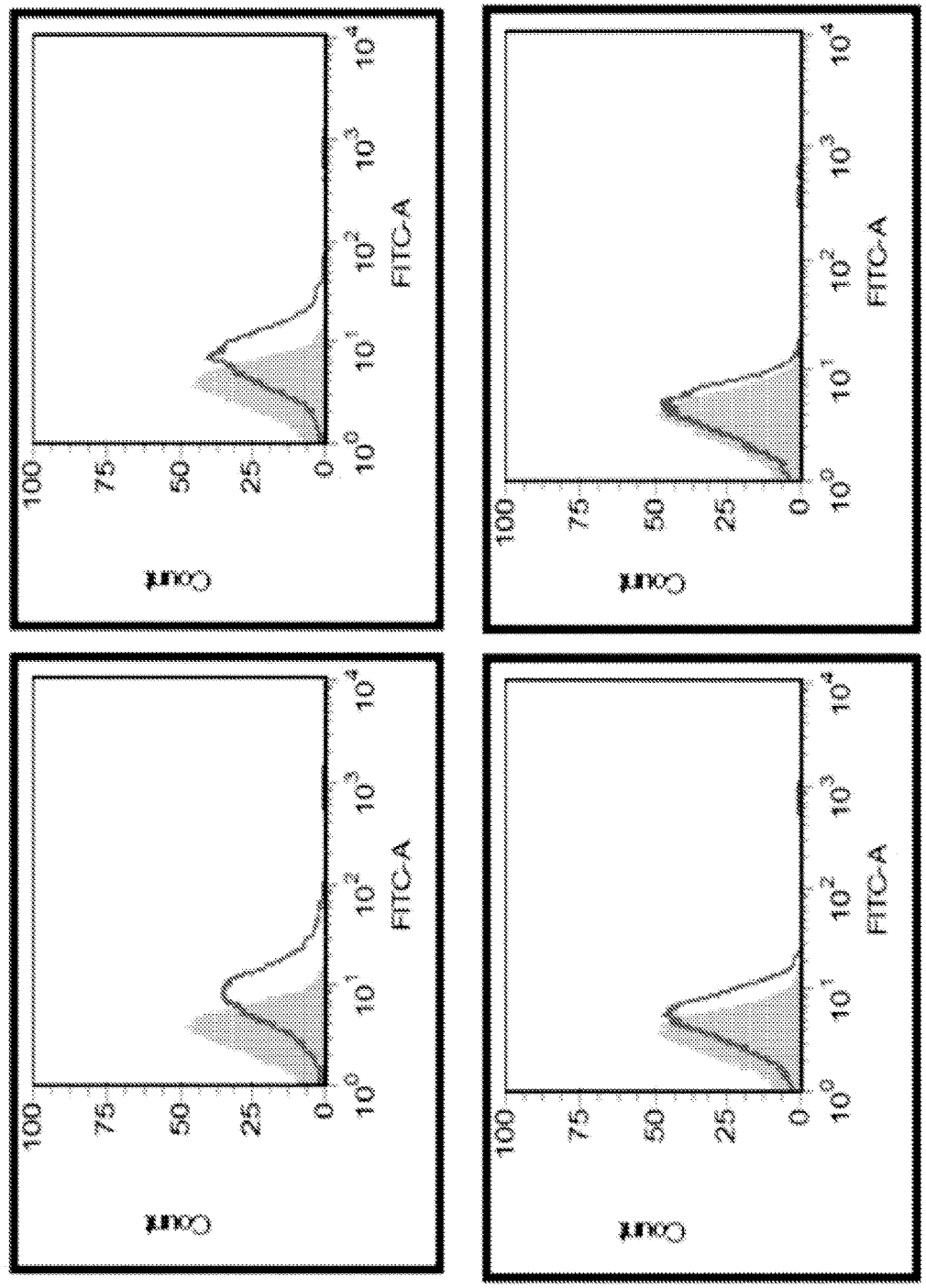
FIG. 3 is a diagram showing the binding of mAb 2H9 to Ramos cells, which express mIgE.FcL (red line), but not mIgE.FcS (shaded histograms). Ramos cells were incubated with 20, 10, 1, and 0.1 µg/ml antibodies on ice for 20 min, followed by staining with FITC-labeled rabbit F(ab¢)2 specific for mouse IgG.
Figure 4:
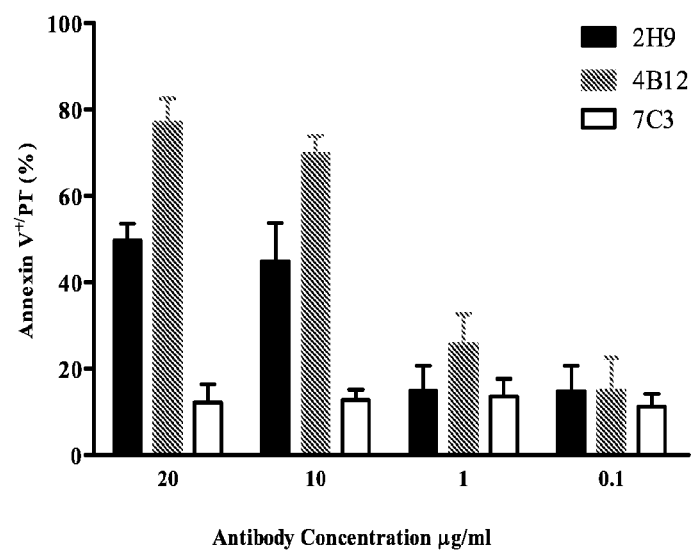
FIG. 4 is a chart showing the induction of apoptosis of mIgE-expressing Ramos cells by mAb 2H9. Monoclonal antibody mAbs 7C3, which is specific for migis-α (the extracellular segment of the C-terminal membrane-anchor peptide of membrane-bound α chain of IgA), was used here as an isotype mAb control, and monoclonal antibody 4B12 (see WO2010/097012) was used as a positive control. Results are shown as mean±SD of triplicates from two independent experiments.
Figure 5:
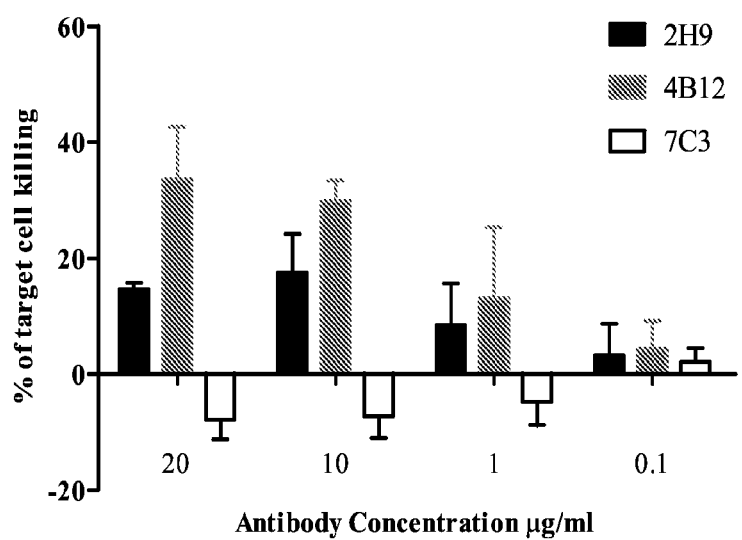
FIG. 5 is a chart showing the induction of NK-cell mediated ADCC of mIgE.FcL-expressing A20 cells by mAb 2H9 at various concentrations. CFSE-positive cells were treated with 2H9 at different concentrations, and then fresh isolated murine NK cells were added at an E:T ratio of 10. Data are means±SD of triplicate samples. 4B12 and 7C3 were used as control mAbs.
Figure 8:
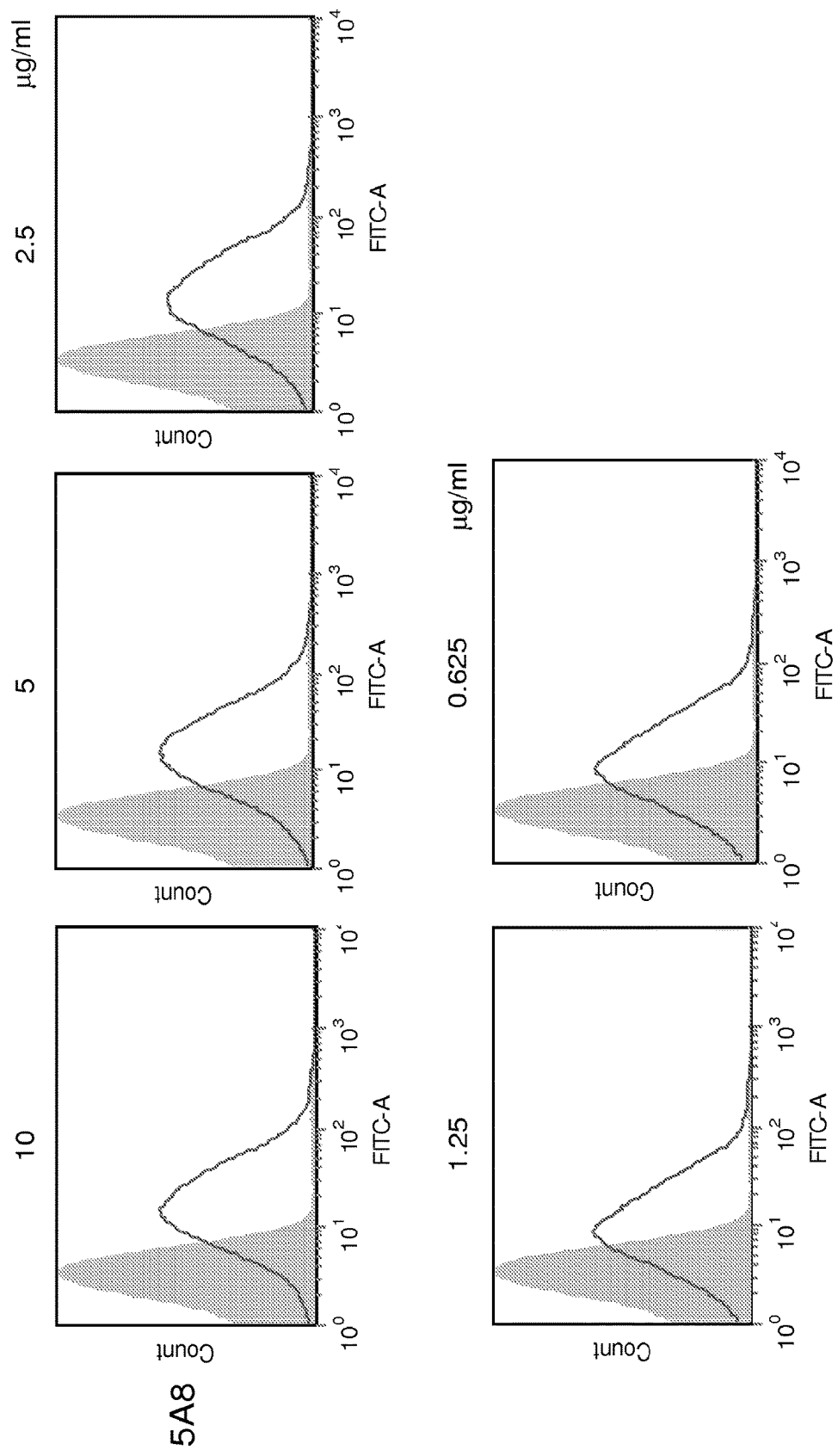
FIG. 8 is a graph showing the binding of mAb 5A8 to Ramos cells expressing mIgE.$Fc_L$, but not to Ramos cells expressing mIgE.$Fc_S$ (shaded histograms). Ramos cells were incubated with 10, 5, 2.5, 1.25, and 0.625 μg/ml of the antibodies as indicated on ice for 20 min, followed by staining with FITC-labeled rabbit F(ab')$_2$ specific for mouse IgG. 4B12 was used as a positive control.
Figure 8:
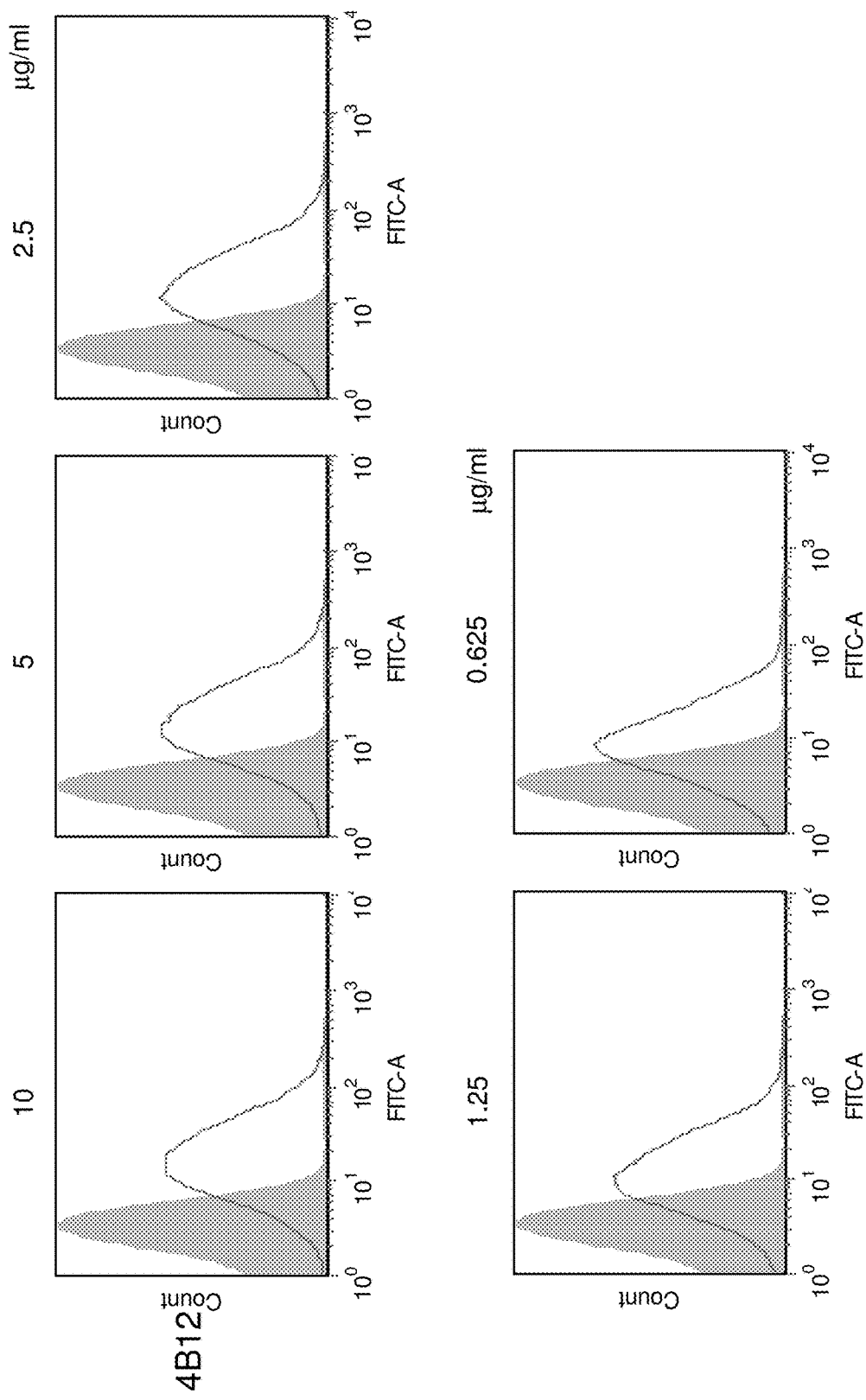
Figure 9:
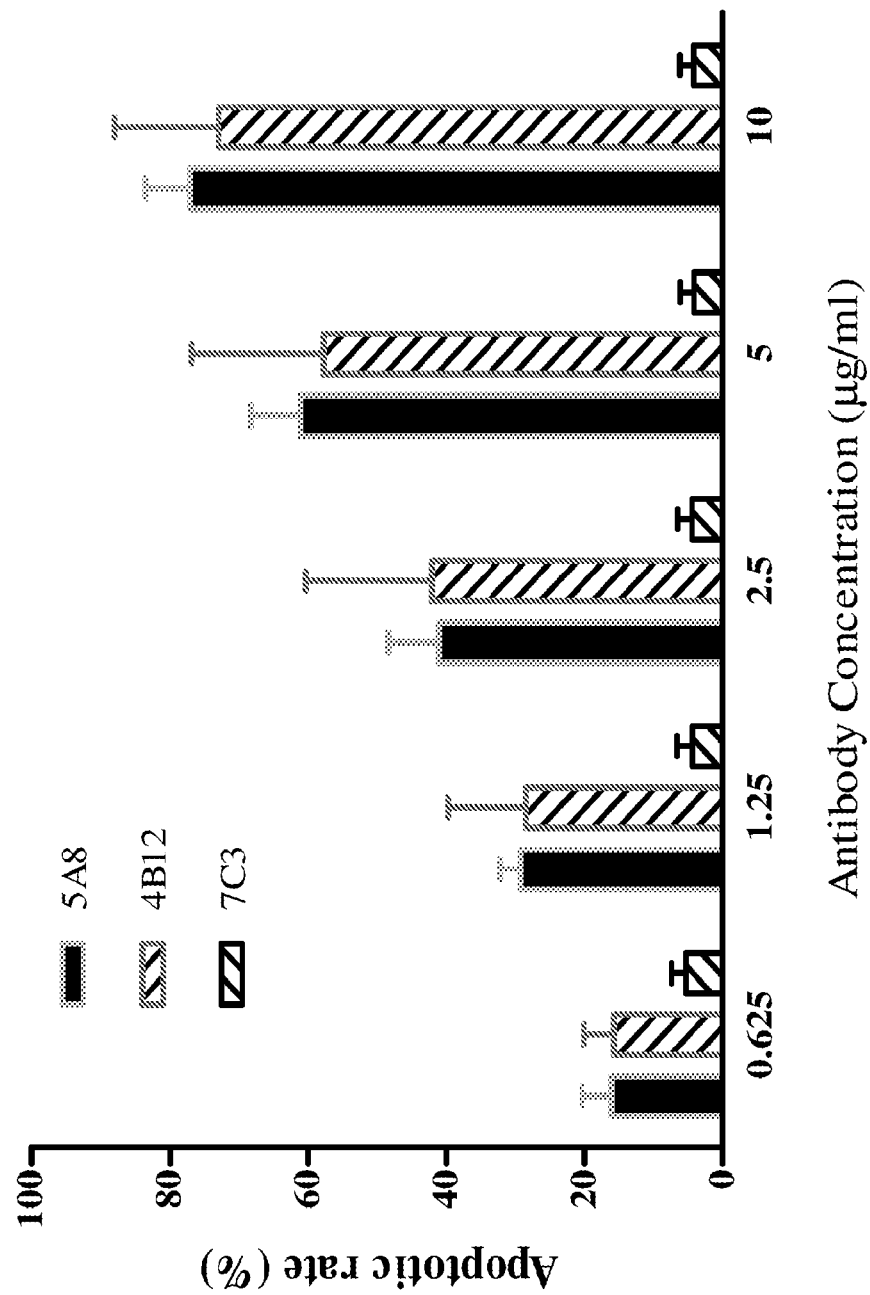
FIG. 9 is a chart showing the induction of apoptosis in mIgE-expression Ramos cells by mAb 5A8. The mAbs 7C3, which is specific to migis-α (the extracellular segment of the C-terminal membrane-anchor peptide of membrane-bound α chain of IgA), was used here as an isotype mAb control, and 4B12 was used as a positive control. Results are mean±SD of triplicates from three independent experiments.
Figure 10:
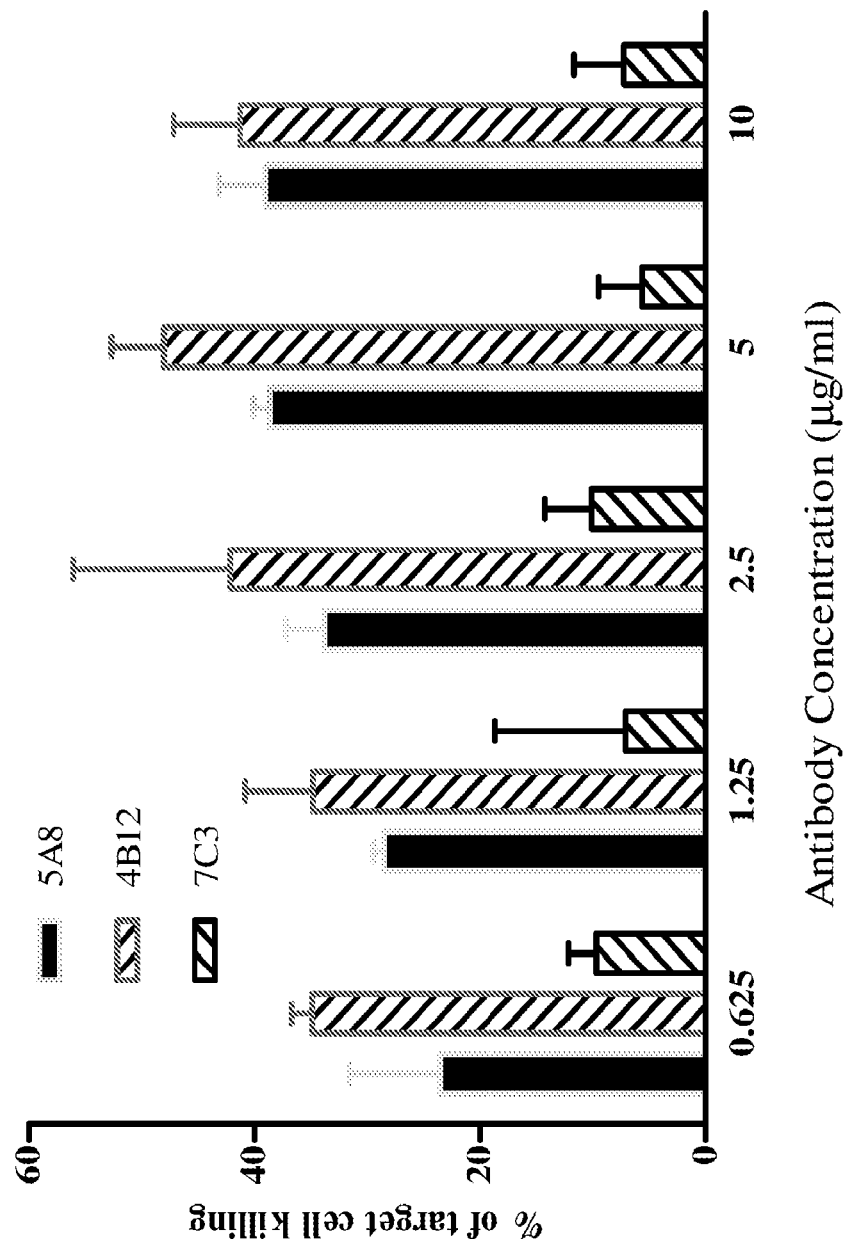
FIG. 10 is a chart showing that 5A8 induced NK-cell mediated ADCC of mIgE.$Fc_L$-expressing A20 cells. CFSE-positive cells were treated with 5A8 at different concentrations as indicated, and then fresh isolated murine NK cells were added at an E:T ratio of 2.5. Data are means±SD of triplicate samples. 4B12 and 7C3 were used as control mAbs.

The anti-IgE antibody described herein can bind to the epitope SVNPGLAGGSAQS (SEQ ID NO:11), or a fragment thereof (e.g., having at least 6 consecutive amino acid residues in SEQ ID NO:11, which are located in both the CH4 domain and the CεmX domain), e.g., P1.17 or P1.18 described in FIG. 2. Such an antibody can be the monoclonal antibody 2H9, or 5A8 described in Example 1 below. The amino acid sequences of the $V_H$ and $V_L$ chains of these antibodies, as well as the heavy chain and light chain complementarity determining domains (CDRs) thereof, are provided in Table 1 below, as well as in FIGS. 6 and 7.

TABLE 1

Amino Acid and Nucleotide Sequences of Antibody 2H9 and Its Binding Epitope

| SEQ ID NO | DESCRIPTION | SEQUENCE |
|---|---|---|
| 1 | 2H9 VH nucleotide sequence | CAGGTGCAAATGCAGCAGCCTGGGGCTGAGCT GGTGAGGCCTGGGGCCTCAGTGAAGATGTCCT GCAGGACTTCTGGCTACACATTTACCAATTAC AATGTACACTGGTTAAAACAGACACCTGGACA GGGCCTGGAATGGATTGGAGGTATGTATCCAG GCAATGATGATATTCTCTACAATCAAAATTTC AAAGACAGGGCCACATTGACTGCAGACAGATC CTCCAGCACAGCCTACATACAACTCAGGAGCC TGACATCTGAGGACTCTGCGGTCTATTACTGT ACAAGATCGGGACTACAGGGGCCCTGGTTTGA TTACTGGGGCCAAGGGACTCTGGTCACTGTCT CTGCA |
| 2 | 2H9 VL nucleotide sequence | GACATCCAGATGACACAGTCTTCATCCTACTT GTCTGTATCTCTAGGAGGCAGAGTCACCATTA GTTGCAGGGCAAGTGACCACATTAATAATTGG TTAGCCTGGTATCAGCAGAAACCAGGAAATGC TCCTAGGCTCTTAATATCTAGTGCAACCAGTT TGGAAACTGGGGTTCCTTCAAGATTCAGTGGC AGTGGATCTGGAAAGGATTACTCTCTCACCAT TATCAGTGTTCAGACTGAAGATGTTGCTACTT ATTACTGTCAACAGTGTTGGATTACTCCATTC ACGTTCGGTTCGGGGACAAAGTTGGAAATAAA A |
| 3 | 2H9 VH amino acid sequence | QVQMQQPGAELVRPGASVKMSCRTSGYTFTNY NVHWLKQTPGQGLEWIGGMYPGNDDILYNQNF KDRATLTADRSSSTAYIQLRSLTSEDSAVYYC TRSGLQGPWFDYWGQGTLVTVSA |
| 4 | 2H9 VL amino acid sequence | DIQMTQSSSYLSVSLGGRVTISCRASDHINNW LAWYQQKPGNAPRLLISSATSLETGVPSRFSG SGSGKDYSLTIISVQTEDVATYYCQQCWITPF TFGSGTKLEIK |
| 5 | 2H9 VL CDR1 | RASDHINNWLA (24-34) |
| 6 | 2H9 VL CDR2 | SATSLET (50-56) |
| 7 | 2H9 VL CDR3 | QQCWITPFT (89-97) |
| 8 | 2H9 VH CDR1 | GYTFTNYNVH (26-35) |
| 9 | 2H9 VH CDR2 | GMYPGNDDILYNQNFKD (50-65) |
| 10 | 2H9 VH CDR3 | SGLQGPWFDY (95-103) |
| 11 | 2H9 binding epitope | SVNPGLAGGSAQS |
| 12 | C-terminus of CH4 shown in FIG. 1 | TVQRAVSVNP |
| 13 | N-terminus of CεmX shown in FIG. 1 | GLAGGSAQSQ |
| 14 | First segment of 2H9 binding epitope (from CH4) | SVNP |
| 15 | Second segment of 2H9 binding epitope (from CεmX) | GLAGGSAQS |

The anti-IgE antibody described herein can bind to the same epitope as 2H9 or 5A8. In some examples, such antibodies can contain the same $V_H$ and $V_L$ chains as antibody 2H9 or 5A8, or the same CDRs therein. See Table 1 above and FIGS. 6 and 7.

Also provided here are functional variants of antibody 2H9 or 5A81. Such functional variants can have essentially the same epitope-binding specificity as mAb 2H9 or 5A8, and exhibits at least 20% (e.g., 30%, 40%, 50%, 60%, 70%, 80%, 90%, or greater) of the activity of inducing apoptosis and/or ADCC in mIge-expression B cells. In some embodiments, a functional variant of 2H9 or 5A8 contains the same regions/residues responsible for antigen-binding as 2H9 or 5A8, such as the same specificity-determining residues in the CDRs or the whole CDRs. The regions/residues that are responsible for antigen-binding can be identified from amino acid sequences of the heavy chain/light chain sequences of 2H9 or 5A8 (Table 1 and FIGS. 6 and 7) by methods known in the art. See, e.g., www.bioinf.org.uk/abs; Almagro, J. Mol. Recognit. 17:132-143 (2004); and Chothia et al., J. Mol. Biol. 227:799-817 (1987).

In addition, determination of CDR regions in an antibody is well known to those skilled in the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

In some examples, a functional variant of 2H9 or 5A8 comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of 2H9 or 5A8, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of 2H9 or 5A8. In other examples, the functional variant of 2H9 or 5A8 comprises the same $V_H$ and $V_L$ CDRs as 2H9 or 5A8.

Alternatively, the functional variant of 2H9 or 5A8 comprises a $V_H$ chain at least 75% (e.g., 80%, 85%, 90%, 95%, or 98%) identical to the $V_H$ chain of 2H9 or 5A8 and a $V_L$ chain at least 75% (e.g., 80%, 85%, 90%, 95%, or 98%) identical to the $V_L$ chain of 2H9 or 5A8.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In other examples, a functional variant of 2H9 or 5A8 comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of 2H9 or 5A8, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of 2H9 or 5A8.

Antibody Preparation

Antibodies capable of binding to the mIgE junction epitopes described herein can be made by any method known in the art. See, for example, Harlow and Lane, (1988) Antibodies: A Laboratory Manual, Cold Spring Harbor Laboratory, New York.

(i) Immunization of Host Animals and Hybridoma Technology

Polyclonal antibodies against the IgE epitopes may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum.

Polyclonal antibodies are generally raised in host animals (e.g., rabbit, mouse, horse, or goat) by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, etc.

Any mammalian animal may be immunized with the antigen for producing the desired antibodies. In general, animals of Rodentia, Lagomorpha, or Primates can be used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Animals are immunized against the antigen, immunogenic conjugates, or derivatives by combining 1 mg or 1 μg of the peptide or conjugate (for rabbits or mice, respectively) with 3 volumes of Freund's incomplete adjuvant.

Animals can be boosted until the titer plateaus by several administrations of antigen mixed with an appropriately amount of Freund's incomplete adjuvant every 4 to 21 days. Animals are boosted with ⅕ to 1/10 the original amount of peptide or conjugate in Freund's complete adjuvant by subcutaneous injection at multiple sites. Seven to 14 days later the animals are bled and the serum is assayed for antibody titer. An appropriate carrier may also be used for immunization. After immunization as above, serum is examined by a standard method for an increase in the amount of desired antibodies. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Over the past two to three decades, a number of methodologies have been developed to prepare chimeric, humanized or human antibodies for human in-vivo therapeutic applications. The most used and proven methodology is to prepare mouse mAbs using hybridoma methodology and then to humanize the mAbs by converting the framework regions of the $V_H$ and $V_L$ domains and constant domains of the mAbs into most homologous human framework regions of human $V_H$ and $V_L$ domains and constant regions of a desirable human γ immunoglobulin isotype and subclass. Many mAbs, such as Xolair, used clinically are humanized mAbs of human γ1, κ isotype and subclass and prepared using this methodology.

In some embodiments, antibodies specific to a target epitope (e.g., a junction epitope between the CH4 and CεmX domains of mIgE) can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method. BIAcore (Pharmacia) may be used to evaluate the activity of the antibody according to the present invention. The binding affinity of the monoclonal antibody can, for example, be determined by the Scatchard analysis of Munson et al., Anal. Biochem., 107:220 (1980).

Applying any of the conventional methods, including those described above, hybridoma cells producing anti-IgE antibodies that bind to epitopes containing residues both in the CH4 and CεmX domains can be identified. For example, antibodies capable of binding to a junction region between the CH4 and CεmX domains but not to the segment from the CH4 domain and/or the CεmX domain can be selected for further characterization.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In addition, the hybridoma cells may be grown in vivo as ascites tumors in an animal. For example, the obtained hybridomas can be subsequently transplanted into the abdominal cavity of a mouse and the ascites are harvested.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention.

(ii) Recombinant Technology

The monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

When the obtained antibody is to be administered to the human body (antibody treatment), a human antibody or a humanized antibody is preferable for reducing immunogenicity. For example, transgenic animals having a repertory of human antibody genes may be immunized with an antigen selected from a protein, protein expressing cells, or their lysates. Antibody producing cells are then collected from the animals and fused with myeloma cells to obtain hybridoma, from which human antibodies against the protein can be prepared. Alternatively, an immune cell, such as an immunized lymphocyte, producing antibodies may be immortalized by an oncogene and used for preparing monoclonal antibodies.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Rev., 130:151-188 (1992).

DNAs encoding the antibodies produced by the hybridoma cells described above can be genetically modified, via routine technology, to produce genetically engineered antibodies. Genetically engineered antibodies, such as humanized antibodies, chimeric antibodies, single-chain antibodies, and bi-specific antibodies, can be produced via, e.g., conventional recombinant technology. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad Sci. USA, 89:4285 (1992); Presta et al., J. Immnol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i. e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 (1991)).

Any of the nucleic acid encoding the anti-IgE antibody described herein (including heavy chain, light chain, or both), vectors such as expression vectors comprising one or more of the nucleic acids, and host cells comprising one or more of the vectors are also within the scope of the present disclosure. In some examples, a vector comprising a nucleic acid comprising a nucleotide sequence encoding either the heavy chain variable region or the light chain variable region of an anti-IgE antibody as described herein. In other examples, the vector comprises nucleotide sequences encoding both the heavy chain variable region and the light chain variable region, the expression of which can be controlled by a single promoter or two separate promoters. Also provided here are methods for producing any of the anti-IgE antibodies as described herein, e.g., via the recombinant technology described in this section.

(iii) Other Technology for Preparing Antibodies

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-MouseΩ and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Alternatively, the anti-IgE antibodies described herein can be isolated from antibody phage libraries (e.g., single-chain antibody phage libraries) generated using the techniques described in McCafferty et al., Nature, 348:552-554 (1990). Clackson et al., Nature, 352:624-628 (1991) and Marks et al., J. Mol Biol., 222:581-597 (1991). Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Antibodies obtained as described herein may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto. The concentration of the antibodies obtained as above may be determined by the measurement of absorbance, Enzyme-linked immunosorbent assay (ELISA), or so on. Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography, such as HPLC, FPLC.

The antibodies can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays.

In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various residues in the binding epitope for the candidate antibody have been replaced (swapped) with sequences from a closely related, but antigenically distinct protein (such as another member of the neurotrophin protein family). By assessing binding of the antibody to the mutant target protein, the importance of the particular antigen fragment to antibody binding can be assessed.

Alternatively, competition assays can be performed using other antibodies known to bind to the same antigen to determine whether an antibody binds to the same epitope (e.g., the 2H9 antibody described herein) as the other antibodies. Competition assays are well known to those of skill in the art.

Further, any of the anti-IgE antibodies obtained from a method known in the art and described herein can be investigated to confirm its ability in inducing apoptosis and/or ADCC in mIgE-expressing B cells following methods known in the art, e.g., the methods described in Examples 3 and 4 below.

Pharmaceutical Compositions and Formulations

After preparation of the anti-IgE antibodies as described herein, a "pre-lyophilized formulation" can be produced. The antibody for preparing the formulation is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. In certain embodiments, the protein is an antibody.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 μm m size.

Use of Anti-IgE Antibodies for Treating IgE-Mediated Diseases

To practice the method disclosed herein, an effective amount of the pharmaceutical composition/formulation described above, containing at least one anti-IgE antibody described herein, can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-IgE antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having an disease mediated by IgE, such as an allergic disease, which include, but not limited to, anaphylaxis, allergic asthma, allergic rhinitis, atopic dermatitis (eczema), dust allergy, insect or reptile venom allergy, food allergy, pollen allergy, and latex allergy. A subject having an IgE-mediated disease can be identified by routine medical examination, e.g., laboratory tests. A subject suspected of having an IgE-mediated disease might show one or more symptoms of the disorder, e.g., allergic responses such as irritation of the nose, sneezing, itching, and redness of the eyes, abdominal pain, bloating, vomiting, diarrhea, itchy and/or swelling of the skin, respiratory reactions (asthmatic reactions), rhinitis, and/or anaphylaxis. A subject at risk for an IgE-mediated disease such as allergy can be a subject having one or more of the risk factors for that disorder. Risk factors for allergy include, but are not limited to, family history, gender, age, immune system, diet habit, and/or living environment.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of the IgE-mediated disease. Alternatively, sustained continuous release formulations of anti-IgE antibody may be appropriate. Various formulations and devices for achieving sustained release are known in the art.

In one example, dosages for an anti-IgE antibody as described herein may be determined empirically in individuals who have been given one or more administration(s) of the antibody. Individuals are given incremental dosages of the antibody. To assess efficacy of the antibody, an indicator of the disease (e.g., allergy) can be followed according to routine practice.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate the IgE-mediated disease, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

For the purpose of the present disclosure, the appropriate dosage of an anti-IgE antibody will depend on the specific antibody (or compositions thereof) employed, the type and severity of the IgE-mediated disease, whether the antibody is administered for preventive or therapeutic purposes, previous therapy, the patient's clinical history and response to the antibody, and the discretion of the attending physician. Typically the clinician will administer an anti-IgE antibody, such as an 2H9, until a dosage is reached that achieves the desired result. Administration of an anti-IgE antibody can be continuous or intermittent, depending, for example, upon the recipient's physiological condition, whether the purpose of the administration is therapeutic or prophylactic, and other factors known to skilled practitioners. The administration of an anti-IgE antibody may be essentially continuous over a preselected period of time or may be in a series of spaced dose, e.g., either before, during, or after developing an IgE-mediated disease.

As used herein, the term "treating" refers to the application or administration of a composition including one or more active agents to a subject, who has an IgE-mediated disease such as an allergic disease, a symptom of the disease, or a predisposition toward the disease, with the purpose to cure, heal, alleviate, relieve, alter, remedy, ameliorate, improve, or affect the disorder, the symptom of the disease, or the predisposition toward the disease.

Examples of IgE-mediated diseases include, but are not limited to, cold-induced urticaria, chronic urticaria, cholinergic urticaria, chronic rhinosinusitis, systemic mastocytosis, cutaneous mastocytosis, allergic bronchopulmonary aspergillosis, recurrent idiopathic angioedema, interstitial cystitis, an eosinophil-associated gastrointestinal disorder, allergic asthma, allergic rhinitis or atopic dermatitis. In some examples, an IgE-mediated disease is an allergic disease, e.g., anaphylaxis, allergic asthma, allergic rhinitis, atopic dermatitis (eczema), dust allergy, insect or reptile venom allergy, food allergy, pollen allergy, and latex allergy.

Alleviating an IgE-mediated disease includes delaying the development or progression of the disease, or reducing disease severity. Alleviating the disease does not necessarily require curative results. As used therein, "delaying" the development of a disease (such as an allergic disease) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability (the risk) of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of an IgE-mediated disease includes initial onset and/or recurrence.

In some embodiments, the anti-IgE antibody (e.g., 2H9, 5A8, or a variant thereof) described herein is administered to a subject in need of the treatment at an amount sufficient to induce apoptosis and/or ADCC effects in mIgE-expressing B cells in the subject, thereby eliminating such B cells at a level of at least 20%, 40%, 60%, 80%, 90%, or greater.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an anti-IgE antibody is administered via site-specific or targeted local delivery techniques. Examples of site-specific or targeted local delivery techniques include various implantable depot sources of the anti-IgE antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., WO 00/53211 and U.S. Pat. No. 5,981,568.

Immunopeptides and Immune Compositions Comprising Such

Also described herein are immunogenic peptides derived from mIgE, particularly the junctions between the CH4 and CϵmX domains of the mIgE. The term "peptide" means a compound in which amino acids are bonded to each other by peptide bond. Preferably, the peptide contains up to 200 amino acid residues, e.g., up to 150 aa, 100 aa, 80 aa, 50 aa, or 25 aa. Alternatively, the peptide can have a molecular weight of about 15-20 kD, or less.

The immunogenic peptide described here comprises at least two segments, the first one being derived from the C-terminus of the CH4 domain and the second one being derived from the N-terminus of the CϵmX domain. The first and second segments, in total, can consist of 6-15 amino acid residues (e.g., 6-12 aa, 6-10 aa, 8-15aa, or 8-10aa) located at the junction of the CH4 and CϵmX domains. In some examples, the first and second segments, in total, have 6, 7, 8, 9, 10, 11, 12, 13, 14, or 15 amino acids in length.

The first segment can comprise the amino acid sequence TVQRAVSVNP (SEQ ID NO:12) or a fragment thereof (e.g., having a deletion of 1, 2, 3, 4, 5, or more residues from the N-terminal end), which is located at the C-terminus of the CH4 domain. In one example, the first segment from the C-terminus of the CH4 domain includes the sequence SVNP (SEQ ID NO:14) or a fragment thereof (e.g., having a deletion of 1, 2, or 3 residues from the N-terminal end).

The second segment can comprise the amino acid sequence GLAGGSAQSQRAPDRVL (SEQ ID NO:35), or a fragment thereof (e.g., having a deletion of 1, 2, 3, 4, 5, or more residues from the C-terminal end). In one example, the second segment includes the amino acid sequence GLAGGSAQS (SEQ ID NO:15), or a fragment thereof (e.g., having a deletion of 1, 2, or 3 residues from the C-terminal end).

In some embodiments, the immunogenic peptide comprises the amino acid sequence SVNPGLAGGSAQS (SEQ ID NO:11), or a fragment thereof, wherein the fragment contains residues from the CH4 domain and residues from the CϵmX domain.

When necessary, the immunogenic peptide described herein can further comprises a third segment that is heterologous to the first and second segment. For example, the third segment is derived from a non-mIgE protein or from a region of an mIgE not consecutive to the first and second segments.

The immunogenic peptides described herein can be prepared by a conventional method, e.g., chemical synthesis or recombinant technology. The peptides may first require chemical modification to improve their half-life in vivo. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2,4,6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

The immunogenic peptide can be used to form immunogenic compositions (e.g., vaccine) for use in eliciting immune responses specific to the peptide, e.g., antibody responses. Methods for preparing immunogenic compositions are well known in the art, e.g., those described above.

For example, methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The immunogenic peptide of this disclosure may be mixed with physiologically acceptable and excipients compatible. Excipients may include, water, saline, dextrose, glycerol, ethanol, and combinations thereof. The vaccine may further contain minor amounts of auxiliary substances such as wetting or emulsifying agents, pH buffering agents, or an adjuvant to enhance the effectiveness of the vaccines. Methods of achieving adjuvant effect for the vaccine include use of agents, such as aluminum hydroxide or phosphate (alum), commonly used as 0.05 to 0.1 percent solutions in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10-95% of the immunogenic peptide described herein.

Articles of Manufacture

In another embodiment of the present disclosure, an article of manufacture is provided which contains any of the pharmaceutical compositions and formulations described herein (e.g., comprising an anti-IgE antibody or an immunopeptide) and provides instructions for its reconstitution and/or use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the formulation and the label on, or associated with, the container may indicate directions for reconstitution and/or use. For example, the label may indicate that the formulation is reconstituted to protein concentrations as described above. The label may further indicate that the formulation is useful or intended for subcutaneous administration. The container holding the formulation may be a multi-use vial, which allows for repeat administrations (e.g., from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/mL. The article of manufacture may further include other materials desirable from a commercial and user standpoint, including other buffers, diluents, filters, needles, syringes, and package inserts with instructions for use.

General Techniques

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

The terms used in this specification generally have their ordinary meanings in the art, within the context of the invention, and in the specific context where each term is used. Certain terms that are used to describe the invention are discussed herein, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Preparation of mAbs Specific to CH4-C•mX Junction of the Long Isoform of Human Membrane-Bound E Chain Hybridoma methodology was employed for the development of mAbs specific to a junction peptide of CH4-CϵmX. The antigen used for immunizing BALB/c mice was a recombinant fusion protein containing the hepatitis B core antigen (HBcAg) inserted with a junction peptide having the amino acid sequence of SVNPGLAGGSAQSQRAPDRVL (SEQ ID NO:25; P1). SEQ ID NO:25 contains 4 amino acid residues, SVNP (SEQ ID NO:14), from the C-terminus of the CH4 domain and 17 amino acid residues, GLAGGSAQSQRAPDRVL (SEQ ID NO:35), from the N-terminus of the CϵmX domain. The goal of this study was to develop mAbs that recognize SVNP and part of GLAGGSAQSQRAPDRVL (SEQ ID NO:35) as essential parts of the antigenic epitope.

Briefly, the coding sequence of a truncated HBcAg (residues 1-149), amplified from the plasmid p3224-3-HBV-core (encoding the full-length HBcAg), was cloned into pET-28a vector (Novagen). The HBcAg-P1 construct was prepared at the DNA level by replacing Pro79 and Ala80 at the MIR by P1. N-terminal linker was GGGGT (SEQ ID NO:36) and the C-terminal linker was GG. The HBcAg-P1 construct contains an N-terminal hexahistidine-tag for purification (45) and was expressed in the E. coli strain BL21.

IPTG-induced large-scale expression of the fusion protein was performed as follows. E. coli cells transformed by the expression constructs noted above were cultured in 0.6 L of Luria Bertani medium (pH 7.0) supplemented with Kanamycin (50 µg/ml) over night. The overnight culture was diluted in 6 L Luria Bertani medium and incubated at 30° C. in a shaker at 220 rpm. When the $OD_{600}$ of the culture reached 0.6-0.8, protein expression was induced with isopropyl-β-D-thiogalactoside (0.1 mM) and the culture was further incubated for 16-18 hrs. The cells were then harvested at 10,000×g at 4° C. for 10 min. The supernatant was discarded, and the pellet was resuspended in 60 ml of lysis buffer (1×PBS, pH7.4, 0.1% NP-40, 5 mM EDTA, 0.5 mg/ml lysozyme) by stirring in an ice-cold waterbath, and the cells were lysed by a single passage at 12,000 lb/in$^2$ through a French pressure cell (Thermo Scientific, Waltham, Mass.). After centrifugation, the proteins in the supernatant were precipitated with ammonium sulfate and the precipitate was resuspended in 20 ml of 1× equilibration buffer, dialyzed against the same buffer, and centrifuged, and the supernatant was recovered. The purification of His-tagged HBcAg via Ni-NTA agarose was performed at room temperature. The purity of recombinant protein was analyzed by SDS-PAGE and the band of identical mobility was further detected by immunoblotting using an anti-HBcAg mAb, clone 13A9 (1:1000 dilution, Santa Cruz Biotechnology, Inc.).

Female BALB/c mice, aged 6-8 weeks old, were immunized three times subcutaneously with the HBcAg-P1 fusion protein prepared as described above without adjuvant at 2-wk intervals. A final boost was given intraperitoneally with 50 µg of HBcAg-P1 in the absence of adjuvant, and 3 days later, the spleen cells from immunized mice were used for generating hybridomas.

Hybridoma cells secreting antibodies with the desired antigen-binding activities were screened as follows. Microtiter plates were coated by incubating with 10 µg/mL of P1 peptide and various other peptides or 1 µg/mL of various recombinant CϵmX-fusion proteins in carbonate buffer, 0.1M, pH 9.6, overnight at 4° C. The wells were blocked with 1% BSA in PBS, pH=7.3 for 1 hour and incubated with the antisera or control antibodies at various dilutions for 1 hour at 37° C. After washing, the ligand-bound antibodies were detected by HRP-conjugated goat anti-mouse IgG, Fcγ fragment specific (Jackson ImmunoResearch) at 1:10,000 and incubated for 1 hour at 37° C., followed by incubation with TMB substrate (Clinical Scientific Products). The OD was determined at 450 nm. Positive clones were selected for further characterization.

A number of exemplary clones, including mAb 2H9 and 5A8, were identified in this study as capable of binding to P1.

The $V_H$ and $V_L$ gene segments of the above noted antibody clones were amplified by PCR from the hybridoma clones secreting the antibody. The gene segments thus obtained were sequenced to determine the $V_H$ and $V_L$ sequences of mAb 2H9 and mAb 5A8, which are shown in FIGS. 6 and 7. The complementarity determining regions of the $V_H$ and $V_L$ regions are underlined.

Example 2

Epitope Mapping of mAb 2H9 mAb 2H9 was subjected to epitope mapping studies as described below. Several peptides representing fragments of the P1 peptide were synthesized and their reactivity to mAb 2H9 was analyzed. The amino acid sequences of these peptides were shown in FIG. 2, panel A. The reactivity to mAb 2H9 of various recombinant proteins, including IgE.CH3-CH4, IgE.Fc-ϵm67, IgG.Fc-ϵm67, HBcAg-P1, and HBcAg-CϵmX, were also analyzed. The segment cm67 contains CϵmX (containing 52 amino acid residues in length; see WO2010/097012) and migis-cpeptide (containing 15 amino acid residues in length), which represents the extracellular segment of the membrane-anchor peptide of 81111 chain. The junction sequences of those recombinant proteins are shown in FIG. 2, panel B. mAbs 47H2 and 4B12, which were respectively described in US2009/0010924 and WO2010/097012, were tested in this study for comparison purposes.

The results obtained from this study are shown in FIG. 2, panel C. It was found that the binding of mAb 2H9 to peptides representing the junction of CH4-CϵmX is gradually diminished by removing the residues derived from the CH4 domain, i.e., S, V, N, and P, from the N-terminal end of P1. The removal of QRAPDRVL (SEQ ID NO:37) from the P1 peptide does not affect the reactivity. These results indicate that the antigenic epitope of mAb 2H9 resides in SVNPGLAGGSAQS (SEQ ID NO:11).

As shown in FIG. 2, panel C, mAb 2H9 does not bind to IgE.CH3-CH4 and bind to IgG.Fc-εm67 much more weakly than to IgE.Fc-εm67. These results indicate that the antigenic epitope of mAb 2H9 does not reside in the CH4 domain alone and that the SVNP residues in CH4 are critical to the binding of mAb 2H9 to its cognate antigenic epitope.

The data shown in FIG. 2 also indicate that the mAbs 47H2 and 4B12 do not bind to SVNPGLAGGSAQS (SEQ ID NO:11), in which the antigenic epitope of 2H9 resides.

Example 3

The Binding of mAbs 2H9 and 5A8 to mIgE-Expressing Ramos Transfectants

The binding of 2H9 and 5A8 to mIgE-expressing B cells and the subsequent effects were studied as follows. Human B cell line Ramos or A20, which were respectively transfected with the long or short isoforms of human mIgE, were employed. These cells were incubated with mAb 2H9 at various concentrations (20, 10, 1, and 0.1 μg/ml) or mAb 5A8 at various concentrations (10, 5, 2.5, 1.25, and 0.625 μg/ml) on ice for 20 minutes and then subjected to flow cytometric analysis. The results obtained from this study, as shown in FIGS. 3 and 8, indicate that both 2H9 and 5A8 can bind to mIgE-expressing Ramos cells.

Example 4

The mAbs 2H9 and 5A8 Induced Apoptosis of mIgE-Expressing Ramos Transfectants The ability of mAb 2H9 and mAb 5A8 of inducing apoptosis of mIgE-expressing B cells was investigated. Stable Ramos transfectants ($5\times10^5$/ml) expressing mIgE, mIgE.FcL, or mIgE.FcS were incubated with purified mAb 2H9 or mAb 5A8 in complete RPMI1640 medium for 1 h at 37° C. mAbs 4B12 and 7C3 were used in this study as controls. Secondary antibody, goat F(ab')2 specific for Fc of human IgG (Jackson ImmunoResearch Laboratories, West Grove, Pa.), was added into the medium at a final concentration of 25 μg/ml and the cultures were incubated for an additional 20 or 24 h at 37° C. The level of apoptosis in the treated cells was determined by detecting phosphatidylserine (PS) exposure (20 h), caspase-3 and poly(ADP-ribose) polymerase (PARP) cleavage (24 h). As shown in FIG. 4 and FIG. 9, both mAb 2H9 and mAb 5A8 successfully induced apoptosis in mIgE-expressing Ramos cells.

Example 5 mAb 2H9 and mAb 5A8 Induced Antibody-Dependent Cellular Cytotoxicity on mIgE-Expressing A20 Transfectants Mouse NK cells were purified from splenocytes by MACS with anti-CD49 (DX5) microbeads (Miltenyi Biotech) according to the manufacturer's instructions. mIgE. FcL-expressing Ramos cells were labeled with CFSE (Invitrogen) in PBS/0.1% BSA for 10 min at 37° C. After three rounds of washes with cold complete RPMI 1640 medium, cells were adjusted to 105 cells/ml. Aliquots of 20,000 labeled cells in 200 μl complete RPMI medium were coated with the mAbs to be tested (including mAb 2H9, 5A8, 4B12, and 7C3) for 30 min at 37° C., and then mixed with purified mouse NK cells at an E/T ratio of 10. After 24 h incubation, the total cells were stained with 2.5 μg/m17-amino actinomycin D (Invitrogen) for 15 min on ice and then analyzed on a FACSCanto II flow cytometer (Becton Dickinson Biosciences). Living target cells were defined as CFSE-positive and PI-negative in a dot-plot analysis. The percentage of lysed target cells at the given E/T ratio was: 100×[(% of live target cells in Ab-independent control-% of live target cells in the sample)/% of live target cells in the Ab-independent control]. The results shown in FIGS. 5 and 10 indicate that both 2H9 and 5A8 induced antibody-dependent cellular cytotoxicity on mIgE-expressing Ramos transfectants.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. An isolated anti-IgE antibody, which binds to the amino acid sequence SVNPGLAGGSAQS (SEQ ID NO:11).

2. The isolated anti-IgE antibody of claim 1, wherein the antibody comprises:
   (i) a heavy chain variable region ($V_H$) that contains a $V_H$ complementarity determining region (CDR) 1 of GYTFTNYNVH (SEQ ID NO:8), a $V_H$ CDR2 of GMYPGNDDILYNQNFKD (SEQ ID NO:9), and a $V_H$ CDR3 of SGLQGPWFDY (SEQ ID NO:10); and
   (ii) a light chain variable region ($V_L$) that contains a $V_L$ CDR1 of RASDHINNWLA (SEQ ID NO:5), a $V_L$ CDR2 of SATSLET (SEQ ID NO:6), and a $V_L$ CDR3 of QQCWITPFT (SEQ ID NO:7).

3. The isolated anti-IgE antibody of claim 1, wherein the antibody comprises:
   (i) a heavy chain variable region ($V_H$) that contains a $V_H$ complementarity determining region (CDR) 1 of GFSLTDYGVN (SEQ ID NO:19), a $V_H$ CDR2 of MIWGDGSTDYNSTL (SEQ ID NO:20), and a $V_H$ CDR3 of NWFAY (SEQ ID NO:21); and
   (ii) a light chain variable region ($V_L$) that contains a $V_L$ CDR1 of SSSVNYMH (SEQ ID NO:22), a $V_L$ CDR2 of DTSKLAS (SEQ ID NO:23), and a $V_L$ CDR3 of QQWSSNPW (SEQ ID NO:24).

4. The isolated anti-IgE antibody of claim 1, wherein the antibody comprises:
   a heavy chain variable region set forth as SEQ ID NO:3 and a light chain variable region set forth as SEQ ID NO:4; or
   a heavy chain variable region set forth as SEQ ID NO:17 and a light chain variable region set forth as SEQ ID NO:18.

5. The isolated anti-IgE antibody of claim 1, wherein the antibody binds to the same epitope as an antibody comprising:
   a heavy chain variable region set forth as SEQ ID NO:3 and a light chain variable region set forth as SEQ ID NO:4; or
   a heavy chain variable region set forth as SEQ ID NO:17 and a light chain variable region set forth as SEQ ID NO:18.

6. The isolated anti-IgE antibody of claim 1, wherein the antibody is a full length antibody or an antigen-binding fragment thereof.

7. The isolated anti-IgE antibody of claim 1, wherein the antibody is a human antibody or a humanized antibody.

8. A pharmaceutical composition comprising an anti-IgE antibody of claim 1, and a pharmaceutically acceptable carrier.

9. An isolated nucleic acid or a nucleic acid set, which encodes or collectively encodes:
   (i) a heavy chain variable region ($V_H$) that contains a $V_H$ complementarity determining region (CDR) 1 of GYTFTNYNVH (SEQ ID NO:8), a $V_H$ CDR2 of GMYPGNDDILYNQNFKD (SEQ ID NO:9), and a $V_H$ CDR3 of SGLQGPWFDY (SEQ ID NO:10); and (ii) a light chain variable region ($V_L$) that contains a $V_L$ CDR1 of RASDHINNWLA (SEQ ID NO:5), a $V_L$ CDR2 of SATSLET (SEQ ID NO:6), and a $V_L$ CDR3 of QQCWITPFT (SEQ ID NO:7).

10. The isolated nucleic acid or nucleic acid set of claim 9, wherein the nucleic acid or nucleic acid set encodes the antibody heavy chain variable region of SEQ ID NO:3 and the antibody light chain variable region of SEQ ID NO: 4.

11. The isolated nucleic acid or nucleic acid set of claim 10, which comprises the nucleotide sequence of SEQ ID NO:1, and the nucleotide sequence of SEQ ID NO: 2.

12. An isolated nucleic acid or a nucleic acid set, which encodes or collectively encodes:

(i) a heavy chain variable region ($V_H$) that contains a $V_H$ complementarity determining region (CDR1) of GFSLTDYGVN (SEQ ID NO:19), a $V_H$ CDR2 of MIWGDGSTDYNSTL (SEQ ID NO:20), and a $V_H$ CDR3 of NWFAY (SEQ ID NO:21); and (ii) a light chain variable region (VL) that contains a $V_L$ CDR1 of SSSVNYMH (SEQ ID NO:22), a $V_L$ CDR2 of DTSKLAS (SEQ ID NO:23), and a $V_L$ CDR3 of QQWSSNPW (SEQ ID NO:24).

13. The isolated nucleic acid or nucleic acid set of claim 12, wherein the nucleic acid or nucleic acid set encodes the antibody heavy chain variable region of SEQ ID NO: 17 and the antibody light chain variable region of SEQ ID NO:18.

14. A vector or vector set comprising a nucleic acid or nucleic acid set of claim 9.

15. The vector or vector set of claim 14, wherein the vector or vector set is an expression vector or expression vector set.

16. A host cell comprising a vector or vector set of claim 14.

17. A vector or vector set comprising a nucleic acid or nucleic acid set of claim 12.

18. The vector or vector set of claim 17, wherein the vector or vector set is an expression vector or expression vector set.

19. A host cell comprising a vector or vector set of claim 17.

20. A method for treating an IgE-associated disease, comprising administering to a subject in need thereof an effective amount of the pharmaceutical composition of claim 8.

21. The method of claim 20, wherein the subject is diagnosed with, suspected of having, or at risk for the IgE-mediated disease.

22. The method of claim 21, wherein the IgE-mediated disease is an allergic disease.

23. The method of claim 22, wherein the allergic disease is selected from the group consisting of anaphylaxis, allergic asthma, allergic rhinitis, atopic dermatitis (eczema), dust allergy, insect or reptile venom allergy, food allergy, pollen allergy, and latex allergy.

* * * * *

SEQUENCE LISTING

```
<160> NUMBER OF SEQ ID NOS: 37

<210> SEQ ID NO 1
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 1
caggtgcaaa tgcagcagcc tggggctgag ctggtgaggc ctggggcctc agtgaagatg     60
```

```
tcctgcagga cttctggcta cacatttacc aattacaatg tacactggtt aaaacagaca    120
cctggacagg gcctggaatg gattggaggt atgtatccag gcaatgatga tattctctac    180
aatcaaaatt tcaaagacag ggccacattg actgcagaca atcctccag cacagcctac     240 atacaactca ggagcctgac atctgaggac tctgcggtct attactgtac aagatcggga    300
ctacaggggc cctggtttga ttactggggc caagggactc tggtcactgt ctctgca       357
```

```
<210> SEQ ID NO 2
<211> LENGTH: 321
<212> TYPE: DNA
<213> ORGANISM: Artificial Sequence
<220> FEATURE:
<223> OTHER INFORMATION: Synthetic Polynucleotide

<400> SEQUENCE: 2
```

```
gacatccaga tgacacagtc ttcatcctac ttgtctgtat ctctaggagg cagagtcacc    60
attagttgca gggcaagtga ccacattaat aattggttag cctggtatca gcagaaacca   120
ggaaatgctc ctaggctctt aatatctagt gcaaccagtt tggaaactgg ggttccttca   180
agattcagtg gcagtggatc tggaaaggat tactctctca ccattatcag tgttcagact   240
gaagatgttg ctacttatta ctgtcaacag tgttggatta ctccattcac gttcggttcg   300
gggacaaagt tggaaataaa a                                              321
```

```
<210> SEQ ID NO 3
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 3
```

```
Gln Val Gln Met Gln Gln Pro Gly Ala Glu Leu Val Arg Pro Gly Ala
 1               5                  10                  15

Ser Val Lys Met Ser Cys Arg Thr Ser Gly Tyr Thr Phe Thr Asn Tyr
             20                  25                  30

Asn Val His Trp Leu Lys Gln Thr Pro Gly Gln Gly Leu Glu Trp Ile
         35                  40                  45

Gly Gly Met Tyr Pro Gly Asn Asp Asp Ile Leu Tyr Asn Gln Asn Phe
     50                  55                  60

Lys Asp Arg Ala Thr Leu Thr Ala Asp Arg Ser Ser Ser Thr Ala Tyr
65                  70                  75                  80

Ile Gln Leu Arg Ser Leu Thr Ser Glu Asp Ser Ala Val Tyr Tyr Cys
                 85                  90                  95

Thr Arg Ser Gly Leu Gln Gly Pro Trp Phe Asp Tyr Trp Gly Gln Gly
            100                 105                 110

Thr Leu Val Thr Val Ser Ala
        115
```

```
<210> SEQ ID NO 4
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 4
```

```
Asp Ile Gln Met Thr Gln Ser Ser Ser Tyr Leu Ser Val Ser Leu Gly
 1               5                  10                  15
```

```
Gly Arg Val Thr Ile Ser Cys Arg Ala Ser Asp His Ile Asn Asn Trp
            20                  25                  30
Leu Ala Trp Tyr Gln Gln Lys Pro Gly Asn Ala Pro Arg Leu Leu Ile
        35                  40                  45
Ser Ser Ala Thr Ser Leu Glu Thr Gly Val Pro Ser Arg Phe Ser Gly
50                  55                  60
Ser Gly Ser Gly Lys Asp Tyr Ser Leu Thr Ile Ile Ser Val Gln Thr
65                  70                  75                  80
Glu Asp Val Ala Thr Tyr Tyr Cys Gln Gln Cys Trp Ile Thr Pro Phe
                85                  90                  95
Thr Phe Gly Ser Gly Thr Lys Leu Glu Ile Lys
            100                 105

<210> SEQ ID NO 5
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 5

Arg Ala Ser Asp His Ile Asn Asn Trp Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 6

Ser Ala Thr Ser Leu Glu Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 7

Gln Gln Cys Trp Ile Thr Pro Phe Thr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 8

Gly Tyr Thr Phe Thr Asn Tyr Asn Val His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic Polypeptide
```

```
<400> SEQUENCE: 9

Gly Met Tyr Pro Gly Asn Asp Asp Ile Leu Tyr Asn Gln Asn Phe Lys
1               5                   10                  15

Asp

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 10

Ser Gly Leu Gln Gly Pro Trp Phe Asp Tyr
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 11

Ser Val Asn Pro Gly Leu Ala Gly Gly Ser Ala Gln Ser
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 12

Thr Val Gln Arg Ala Val Ser Val Asn Pro
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Gly Leu Ala Gly Gly Ser Ala Gln Ser Gln
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 14

Ser Val Asn Pro
1

<210> SEQ ID NO 15
<211> LENGTH: 9
<212> TYPE: PRT
<213> ORGANISM: Artificial Sequence
<220> FEATURE:
<223> OTHER INFORMATION: Synthetic Polypeptide
```

<400> SEQUENCE: 15

Gly Leu Ala Gly Gly Ser Ala Gln Ser
1               5

<210> SEQ ID NO 16
<211> LENGTH: 160
<212> TYPE: PRT
<213> ORGANISM: Artificial Sequence
<220> FEATURE:
<223> OTHER INFORMATION: Synthetic Polypeptide

<400> SEQUENCE: 16

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Leu Ala Gly
            100                 105                 110

Gly Ser Ala Gln Ser Gln Arg Ala Pro Asp Arg Val Leu Cys His Ser
        115                 120                 125

Gly Gln Gln Gln Gly Leu Pro Arg Ala Ala Gly Gly Ser Val Pro His
    130                 135                 140

Pro Arg Cys His Cys Gly Ala Gly Arg Ala Asp Trp Pro Gly Pro Pro
145                 150                 155                 160

<210> SEQ ID NO 17
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 17

Gln Val Gln Leu Lys Gln Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Thr Leu Lys
    50                  55                  60

Ser Arg Leu Ser Ile Ser Lys Asp Asn Ser Lys Ser Gln Val Phe Leu
65                  70                  75                  80

Lys Ile Asn Ser Leu Gln Thr Asp Asp Thr Ala Arg Tyr Tyr Cys Ala
                85                  90                  95

Leu Asn Trp Phe Ala Tyr Trp Gly Gln Gly Thr Leu Val Thr Ala Ala
            100                 105                 110

Ala

-continued

```
<210> SEQ ID NO 18
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 18

Asn Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 19

Gly Phe Ser Leu Thr Asp Tyr Gly Val Asn
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 20

Met Ile Trp Gly Asp Gly Ser Thr Asp Tyr Asn Ser Thr Leu
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 21

Asn Trp Phe Ala Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22
```

Ser Ser Ser Val Asn Tyr Met His
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 23

Asp Thr Ser Lys Leu Ala Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 24

Gln Gln Trp Ser Ser Asn Pro Trp
1               5

<210> SEQ ID NO 25
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 25

Ser Val Asn Pro Gly Leu Ala Gly Gly Ser Ala Gln Ser Gln Arg Ala
1               5                   10                  15

Pro Asp Arg Val Leu
            20

<210> SEQ ID NO 26
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 26

Val Asn Pro Gly Leu Ala Gly Gly Ser Ala Gln Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 27

Asn Pro Gly Leu Ala Gly Gly Ser Ala Gln Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Polypeptide

```
<400> SEQUENCE: 28

Pro Gly Leu Ala Gly Gly Ser Ala Gln Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 29

Ser Pro Gly Lys Gly Leu Ala Gly Gly Ser Ala Gln Ser
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 30

Gly Gly Gly Gly Thr Leu Ala Gly Gly Ser Ala Gln Ser
1               5                   10

<210> SEQ ID NO 31
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 31

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Gly Gln Leu Gly Leu Trp Phe Ala Tyr Trp Gly Gln Gly
            100                 105                 110

Thr Leu Val Thr Val Ser Ala
        115

<210> SEQ ID NO 32
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 32

Asp Ile Gln Met Thr Gln Ser Ser Ser Tyr Leu Ser Val Ser Leu Gly
1               5                   10                  15
```

```
Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105

<210> SEQ ID NO 33
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 33

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asn Trp Phe Ala Tyr Trp Gly Gln Gly Thr Leu Val Thr Ala Ala
            100                 105                 110

Ala

<210> SEQ ID NO 34
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 34

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95
```

```
<210> SEQ ID NO 35
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 35

Gly Leu Ala Gly Gly Ser Ala Gln Ser Gln Arg Ala Pro Asp Arg Val
1               5                   10                  15
Leu

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

Gly Gly Gly Gly Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 37

Gln Arg Ala Pro Asp Arg Val Leu
1               5
```